United States Patent [19]

Kanbara et al.

[11] Patent Number: 4,870,950

[45] Date of Patent: Oct. 3, 1989

[54] ENDOSCOPE SYSTEM

[76] Inventors: Kouji Kanbara, 1-12-6-205, Minamiohsawa; Kenichi Kikuchi, Olympus Daini Ishikawaryo, 2974-24 Ishikawa-cho, both of Hachioji-shi, Tokyo; Yoshihito Shimizu, 3528-1-102, Kamitsuruma, Sagamihawa-shi, Kanagawa-ken; Shinichiro Hattori, 5-9-32, Tamagawa,cho, Akishima-shi, Tokyo; Yoshikazu Tojo, Olympus Kyoudojutaku 145, 7-14-11, Ohwada-cho; Akira Hasegawa, Hachioji, 560-11, Kitano-cho, both of Hachioji-shi, Tokyo; Tatsuya Yamaguchi, Hinoshihirayamadaijutaku 106, 6-7-8, Asahigaoka, Hino-shi, Tokyo; Takashi Tsukaya, 888-11, Katakura-cho, Hachioji-shi, Tokyo; Kazunari Kobayashi, 1405-19, Katakura-cho, Hachioji-shi, Tokyo; Masanao Murata, Mezondonoabamu Hachioji 107, 560-11, Kitano-cho, Hachioji-shi, Tokyo; Tsutomu Yamamoto, Takao Pakuhaitsu B-705, 1231-19, Hatsusawa-cho, Hachioji-shi, Tokyo; Takeaki Nakamura, 6-9-8, Asahigaoka, Hino-shi, Tokyo, all of Japan

[21] Appl. No.: 216,600

[22] Filed: Jul. 8, 1988

[30] Foreign Application Priority Data

| Jul. 8, 1987 | [JP] | Japan | 62-105669 |
| Jul. 9, 1987 | [JP] | Japan | 62-169780 |
| Jul. 17, 1987 | [JP] | Japan | 62-177305 |
| Jul. 29, 1987 | [JP] | Japan | 62-115936 |
| Apr. 1, 1988 | [JP] | Japan | 63-081801 |

[51] Int. Cl.⁴ .................................................. A61B 1/06
[52] U.S. Cl. .......................................... 128/6; 358/98
[58] Field of Search ..................... 128/4, 6; 358/98

[56] References Cited

U.S. PATENT DOCUMENTS

| 3,016,785 | 1/1962 | Kanapy . |
| 4,154,502 | 5/1979 | Siegmund . |
| 4,618,884 | 10/1986 | Nagasaki ............................. 358/98 |
| 4,621,618 | 11/1986 | Omagari ................................. 128/6 |

FOREIGN PATENT DOCUMENTS

| 54-107746 | 8/1979 | Japan . |
| 55-143125 | 11/1980 | Japan . |
| 56-11029 | 2/1981 | Japan . |
| 57-49208 | 3/1982 | Japan . |
| 58-168013 | 10/1983 | Japan . |
| 58-168015 | 10/1983 | Japan . |
| 59-71024 | 4/1984 | Japan . |
| 60-53919 | 3/1985 | Japan . |
| 62-80605 | 4/1987 | Japan . |

OTHER PUBLICATIONS

*Fiber Optics Principles and Applications*, N. S. Kapany, Optics Technoloy, Inc., Palo Alto, Calif., Academic Press, 1967, pp. 88–99.

*Primary Examiner*—William H. Brieb

[57] ABSTRACT

This endoscope system is provided with an endoscope and an image receiving apparatus to be fitted to the eyepiece part of this endoscope. The endoscope has an elongate insertable part, an objective optical system provided in the tip part of the insertable part, an eyepiece part provided on the rear end side of the insertable part and an image guide consisting of a fiber bundle transmitting the image formed by the objective optical system to the eyepiece part. The image receiving apparatus has an image receiving part of many pixels on which the image from the eyepiece part is formed. Further, the endoscope system is provided with a vibrating apparatus relatively vibrating the image formed on the image receiving part and the image receiving part. The image receiving apparatus is a television camera, co-viewing apparatus or electronic still camera.

26 Claims, 22 Drawing Sheets

FIG. 6
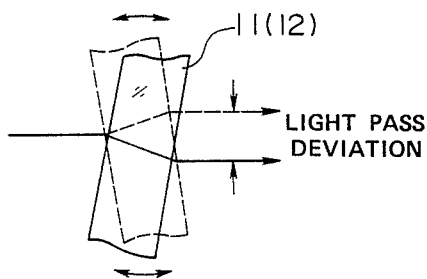
FIG. 7    FIG. 8
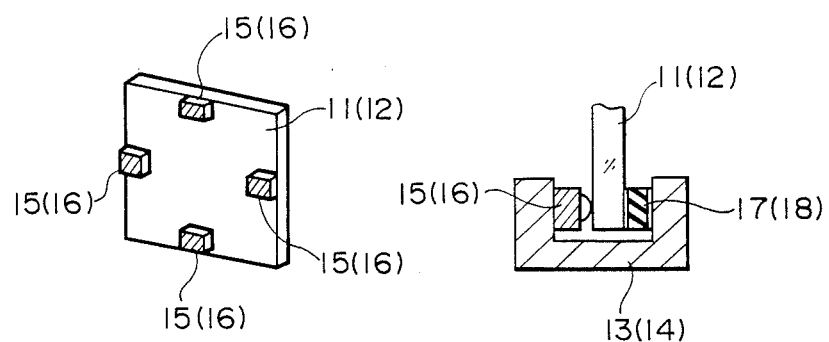

FIG.15(A)     FIG.15(B)
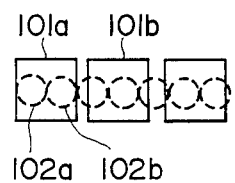   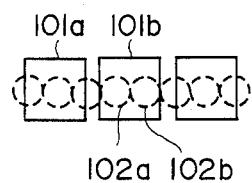
FIG.16
|R|G|B|R|G|B|

ENDOSCOPE SYSTEM

BACKGROUND OF THE INVENTION

1. Field of the Invention

This invention relates to an endoscope system having an image receiving part of many pixels such as a television camera or co-viewing apparatus fitted to an eyepiece part of an endoscope having an image guide with a fiber bundle.

2. Related Art Statement

Recently, an endoscope has recently been used whereby an organ within a body cavity or an interior of a mechanical structure can be observed with an elongated insertable part inserted into the body cavity or, as required, various curing treatments can be made by using treating tools inserted through a treating tool channel.

As in the above mentioned endoscope, there is a fiber scope wherein an object image is transmitted by an image guide having a fiber bundle from an objective lens in a tip part of an insertable part to en eyepiece lens in an eyepiece part and can be observed with a naked eye.

In the above-mentioned fiber scope, television camera connected to the eyepiece part is provided with a solid state imaging device so that a number of persons can simultaneously observe the image. The solid state imaging device is employed as an imaging means or co-viewing apparatus having another image guide.

Now, in the above mentioned fiber scope, as shown, for example, in FIG. 31, an image guide 530 is formed by substantially and closely bundling up (i.e., about several tens of thousands of optical fibers 531 within a diameter of about 10 $\mu$m.) for forming respective pixels 541 and therefore producing mesh patterns on the boundaries of the respective fibers 531. On the other hand, such solid state imaging device such as a CCD, BBD or SID is used. As shown, for example, in FIG. 32, in such a solid state imaging device 540, many light receiving regions forming the respective pixels 541 are arranged regularly in the form of a matrix. Therefore, there are problems in that, when an image transmitted by the above mentioned image guide 530 is imaged by the solid state imaging device 540, moiré fringes are produced by the arrangement of the fibers and arrangement of the pixels of the solid state imaging device and the picture quality will deteriorate.

In other words, as shown in FIG. 33, as the respective pixels 541 of the solid state imaging device are larger than the respective fibers 531 of the image guide and the spatial sampling frequency by the pixels 541 is smaller than the spatial frequency of the image guide, the nyquist limit as of the imaging system is exceeded and a false signal is generated.

Where a color filter array to obtain a simultaneous type color signal is provided on the front surface of the solid state imaging device, moiré fringes will be produced even by the regular arrangement of the respective filters of this color filter array and the arrangement of the fibers.

There is already suggested a means for preventing the generation of such moiré fringes wherein such low pass filter as a crystal filter having double refractive actions is arranged between the image guide and solid state imaging device.

An example of an endoscope apparatus provided with such low pass filter is shown in FIG. 34 wherein, within an endoscope insertable part 501, an image guide 530 consisting of a fiber bundle is extended, an objective lens 503 is arranged as opposed to the entrance end at the tip of the image guide 530 and an eyepiece lens 504 is arranged as opposed to the exit end of the image guide 530. Therefore, in the case of an eye observation, the image of an observed object 505 can be observed through this eyepiece lens 504.

Also, in order to pick up an image with a video camera, a television camera unit 507 is removably fitted as an adapter to an observing part 506 containing an eyepiece lens 504 and is provided with a photographing lens 508, a plurality of low pass filters 509 and a solid state imaging device 540 consisting of a CCD so that an output signal of the solid state imaging device 540 may be processed by a camera controlling unit 511 to make a television signal which will be displayed on a monitor 512.

The plurality of low pass filters 509 inserted between the photographing lens 508 and solid state imaging device 540 are formed of such double refractive filters as quartz plates or diffractive lattice filters utilizing a diffractive action.

As shown in FIG. 32, in case the pitch arrangement in the x direction of the light receiving region of the solid state imaging device 540 is 17 $\mu$m. and the pitch arrangement in the y direction is 26 $\mu$m., in the spatial frequency region shown in FIG. 35, the frequency of moiré fringes will be 30 fringes/mm. in the x direction and 20 fringes/mm. in the y direction and no spatial frequency higher than this frequency will be able to be reproduced in the respective directions. Therefore, by passing through quartz plates 509 having such double refractive actions as are shown in FIG. 36 and having a response characteristic showing a trap frequency at 30 fringes/mm. as shown in FIG. 37, the generation of moiré fringes in the x direction can be controlled.

However, in the endoscope apparatus of the related art shown in FIG. 34, as moiré fringes are not generated in one direction but are generated in a plurality of directions, it is necessary to provide many or usually four or more low pass filters 509 having the optical axis set to be able to erase moiré fringes in the respective directions. Therefore, there is a defect in that the television camera unit 507 becomes large in size. More particularly in case this television camera unit 507 is to be provided as an adapter, it must be as small and light as possible. Therefore, there are defects in that the number of the low pass filters which can be contained will be limited and the moiré fringes will not be able to be well controlled. Further, there are defects in that the double refractive filters when used as the low pass filters 509 are so expensive that, if many of them are provided, the cost of the entire apparatus will be high.

Also, there are problems in that, if many low pass filters are provided, the contrast is reduced and the resolution deteriorates.

As shown, for example, in the publication of a Japanese patent application laid open No. 71024/1984, removal of moiré fringe components with an electric filter from a picture image signal from a solid state imaging device has been suggested. However, there is a problem in that the circuit formation becomes complicated.

Also, in case a co-viewing apparatus is connected to the above mentioned eyepiece part, moiré fringes will be produced by the arrangement of the fibers of the image guide within the fiber scope and the arrangement of the fibers of the image guide within the co-viewing apparatus.

As a means of preventing the generation of such moiré fringes, it is suggested as shown in the publications of Japanese patent applications laid open Nos. 143125/1980 and 11029/1981 to provide low pass filters between the end surface of an image guide of a fiber scope and the end surface of an image guide of a displaying apparatus. However, there are problems in that, in such a case, the same as in the case of the above described television camera, the structure will be complicated, large and expensive.

By the way, there is known a technique of vibrating the objective side end surface of the image guide of a fiber scope or the objective optical system and the eyepiece side end part of the image guide or the eyepiece optical system in the direction intersecting at right angles with the optical axis in order to improve the resolving power. It is mentioned in the respective publications of Japanese patent applications laid open Nos. 168013/1983, 168015/1983, 53919/1985 and 80605/1987 and a Japanese utility model application laid open No 49208/1982, in U.S. Pat. Nos. 3,016,785 and 4,154,502 and in "Fiber Optics" by New York Academic Press, 1967. However, the prevention of the generation of moiré fringes produced by the eyepiece part of a fiber scope and an image receiving means connected to this eyepiece part is not considered in any of these references.

OBJECTS AND SUMMARY OF THE INVENTION

An object of the present invention is to provide an endoscope system whereby the generation of moiré fringes by the eyepiece end of an image guide and an image receiving part of many pixels can be prevented with a simply formation.

Another object of the present invention is to provide an endoscope system whereby the generation of moiré fringes can be prevented without making the apparatus large.

Another object of the present invention is to provide an endoscope system whereby the generation of moiré fringes can be prevented and which is high in durability.

Another object of the present invention is to provide an endoscope system whereby the number of low pass filters for erasing moiré fringes can be reduced and moiré fringes can be erased well.

Another object of the present invention is to provide an endoscope system whereby the generation of moiré fringes can be prevented without reducing the resolving power.

The endoscope system of the present invention is provided with an endoscope and an image receiving means fitted to the eyepiece part of this endoscope. The above mentioned endoscope has an elongated insertable part, an objective optical system provided in the tip part of the above mentioned insertable part, an eyepiece part provided on the rear end side of the above mentioned insertable part and an image transmitting means consisting of a fiber bundle transmitting to the above mentioned eyepiece part an image formed by the above mentioned objective optical system. The above mentioned image receiving means has an image receiving part of many pixels in which an image from the above mentioned eyepiece part is formed. Further, the endoscope system is provided with a vibrating means for relatively vibrating an image formed in the image receiving part and the above mentioned image receiving part which is a television camera, co-viewing apparatus or electronic still camera.

The other features and advantages of the present invention will become apparent enough with the following explanation.

BRIEF DESCRIPTION OF THE DRAWINGS

FIGS. 1 to 8 relate to the first embodiment of the present invention.

FIG. 1 is a perspective view of an endoscope.

FIG. 2 is an explanatory view showing the formation of an endoscope system in which a co-viewing apparatus is fitted to an endoscope.

FIG. 3 is an explanatory view showing the formation of an endoscope system in which a television camera is fitted to an endoscope.

FIG. 4 is an explanatory view showing the formation of an endoscope system in which an electronic still camera is fitted to an endoscope.

FIG. 5 is an explanatory view showing the formation of an endoscope system in which a still camera is fitted to an endoscope.

FIG. 6 is an explanatory view showing that the light path of an entering light deviated by a vibrating transparent plate.

FIG. 7 is a perspective view showing a piezoelectric vibrator used to vibrate the transparent plate.

FIG. 8 is a cross-sectional view showing a magnified transparent plate holding part.

FIGS. 10 to 16 relate to a third embodiment of the present invention.

FIG. 11 is a block diagram showing an example of a control circuit driving a bimorph.

FIG. 12 is an explanatory view showing a color filter array.

FIG. 13 is a timing chart for explaining the operation of a bimorph in a field accumulating mode.

FIG. 14 is a timing chart for explaining the operation of a bimorph in a field accumulating mode.

FIGS. 15(A) and (B) are explanatory views showing relative position relations between pixels of a solid state imaging device and fibers.

FIG. 16 is an explanatory view showing another example of a color filter array.

FIG. 17 is an explanatory view showing the formation of an endoscope system.

FIG. 18 is an explanatory view showing the relations between the vibrating direction of an image guide and the double-refracting direction of a low pass filter.

FIG. 19 is an explanatory view showing the formation of a lecture scope.

FIG. 20 is an explanatory view showing the manner of vibrating an image guide.

FIG. 21 is an explanatory view showing a response characteristic when an image guide is vibrated.

FIG. 26 is an explanatory view showing the scheme of an observed image transmitting system.

FIG. 27 is a perspective view showing ultrasonic motors and an image guide.

DETAILED DESCRIPTION OF PREFERRED EMBODIMENTS

FIGS. 1 to 8 show the first embodiment of the present invention.

Figure 1:
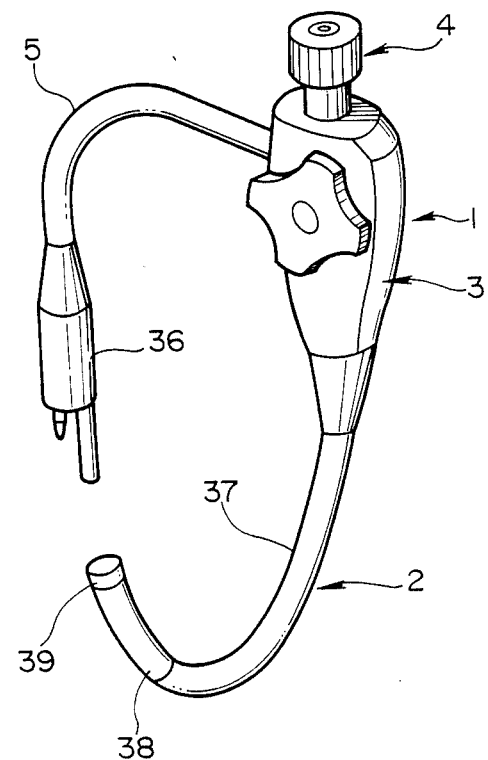

As shown in FIG. 1, an endoscope 1 in this embodiment comprises an elongate, for example, flexible insertable part 2, a thick operating part 3 connected to the rear end of this insertable part, an eyepiece part 4 connected to the rear end of this operating part 3 and a light guide cable 5 extended out of the side of the above mentioned operating part 3. The above mentioned light guide cable 5 is provided at the end with a connector 36 removably connected to a light source apparatus.

The above mentioned insertable part 2 is formed of a flexible part 37 and a curvable part 38 and rigid tip part 39 connected in turn to the tip of this flexible part 37.

An observing optical system transmitting an object image from the tip part 39 of the insertable part 2 to the eyepiece part 4 through an optical fiber bundle is provided within the above mentioned insertable part 2. In other words, an image forming objective lens system 6 is arranged within the tip part 39 of the above mentioned insertable part 2 and an image guide 7 formed of a fiber bundle is inserted through the insertable part 2 so that its tip surface may be located in the position in which an optical image is formed by this objective lens system 6. An eyepiece lens system 8 is provided as opposed to the rear end surface of the above mentioned image guide 7 within the above mentioned eyepiece part 4. The image formed on the tip surface of the above mentioned image guide 7 by the above mentioned objective lens system 6 is transmitted to the eyepiece part 4 side by this image guide 7 and is observed through the eyepiece lens system 8 from this eyepiece part 4.

On the other hand, a light guide 9 for transmitting an illuminating light is inserted through the above mentioned insertable part 2 and curved on the base side within the operating part 3. The light guide is inserted through the above mentioned light guide cable 5 and connected to a connector 36 provided at the tip of this light guide cable 5. When this connector 36 is connected to a light source apparatus not illustrated, an illuminating light will enter the entrance end of the above mentioned light guide 9, will be led to the tip part 39 of the insertable part 2 by the above mentioned light guide 9, will be emitted out of the exit end of this light guide 9 and will be radiated on the forward object side through a light distributing lens 10 arranged as opposed to this exit end.

Now, such transparent plate 11 as a thin glass plate is arranged on a light path of the observing optical system between the above mentioned image forming objective lens system 6 and the front end surface of the image guide 7 to be the image forming position. Also, a transparent plate 12 is arranged on a light path of the observing optical system between the rear end surface of the above mentioned image guide 7 and the eyepiece lens system 8. The above mentioned transparent plates 11 and 12 are contained respectively within frames 13 and 14 and are supported respectively by the above mentioned frames 13 and 14 through respective piezoelectric vibrators 15 and 16 contacting four places on the vertical and horizontal peripheral edges on one surface and respective dampers 17 and 18 contacting the peripheral edges on the other surface as shown in FIGS. 7 and 8. As shown in FIG. 8, the respective piezoelectric vibrators 15 and 16 are secured respectively to the frames 13 and 14 and respectively support the transparent plates 13 and 14 through hemispherical members.

Figure 2:
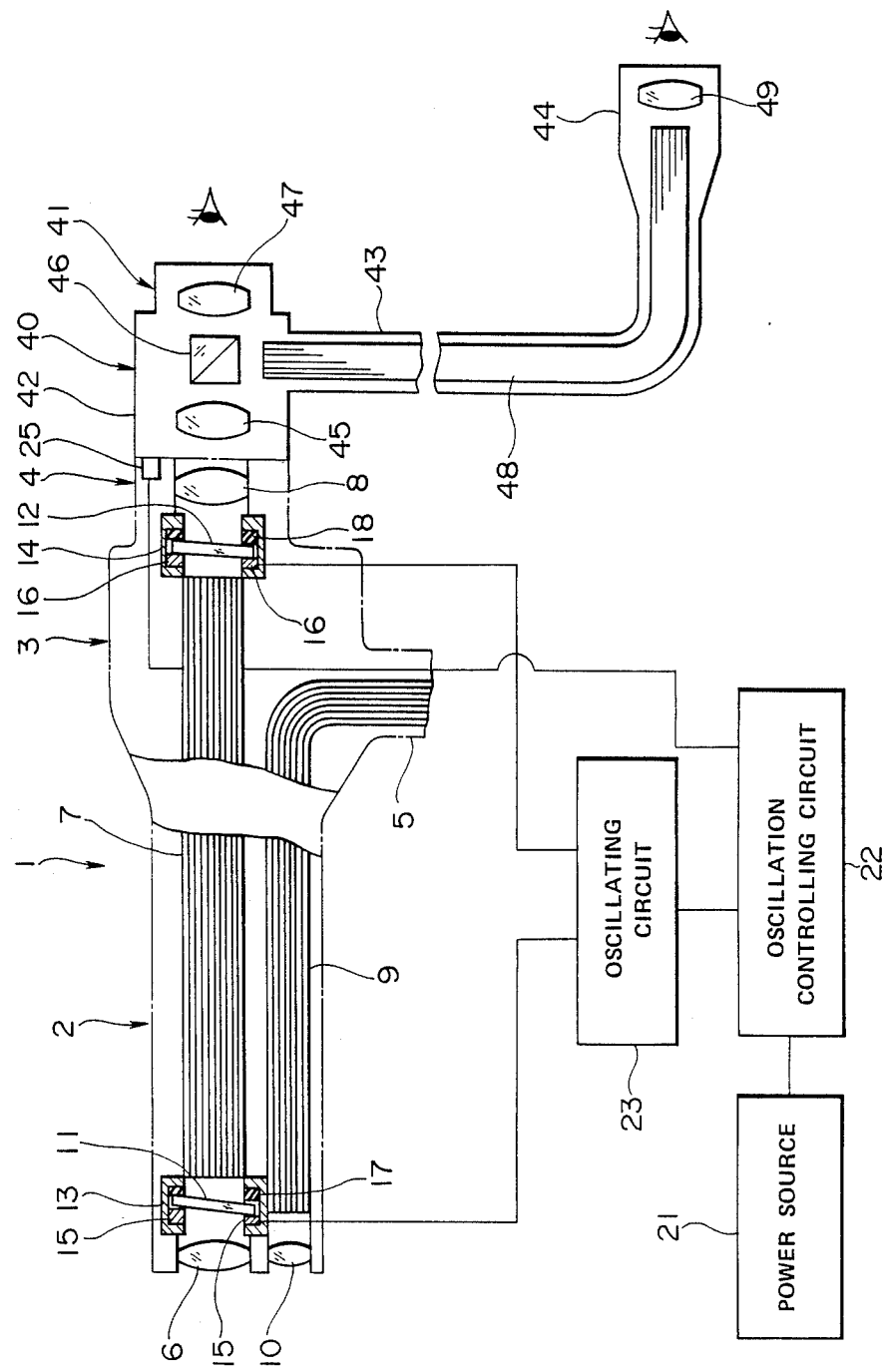

As shown in FIG. 2, the above mentioned piezoelectric vibrators 15 and 16 are driven by an oscillating circuit 23 connected to a power source 21 through an oscillation controlling circuit 22. The above mentioned respective piezoelectric vibrators 15 and 16 are arranged opposite from each other (for example, vertically opposed from each other) can be vibrated so as to vary the thickness in the reverse phase by the application of an alternating current voltage from the above mentioned oscillating circuit. By this vibration, the transparent plates 11 and 12 will be vibrated as indicated by the arrows in FIG. 6 each with the center as a fulcrum. The above mentioned both transparent plates 11 and 12 will be vibrated with the same vibration amount as synchronized. As shown in FIG. 6, by the vibration of the above mentioned transparent plates 11 and 12, the light path will be periodically deviated. By the way, the deviation of the above mentioned light path is set at such predetermined amount as 1 pitch of the arrangement of the fibers forming the image guide 7 on both sides from the center.

When an alternating current voltage from the above mentioned oscillating circuit 21 is applied, the piezoelectric vibrators 15 and 16 in the horizontal direction will also vibrate respectively the transparent plates 11 and 12 as properly related with those in the above mentioned vertical direction. In such vibrating state as is shown, for example, in FIG. 6, the phase of the applied voltage will be controlled so as to make such vibrating mode that, in case the transparent plates 11 and 12 become just vertical, the vibration in the horizontal direction will be maximum and the light path will be deviated by a predetermined amount. By the way, the transparent plates 11 and 12 will be vibrated by the same vibration amount as synchronized even in the vibration in the horizontal direction.

By the way, these vibrations may be of a frequency higher than that at which overlapped images by a residual image can be observed in the sight.

Figure 3:
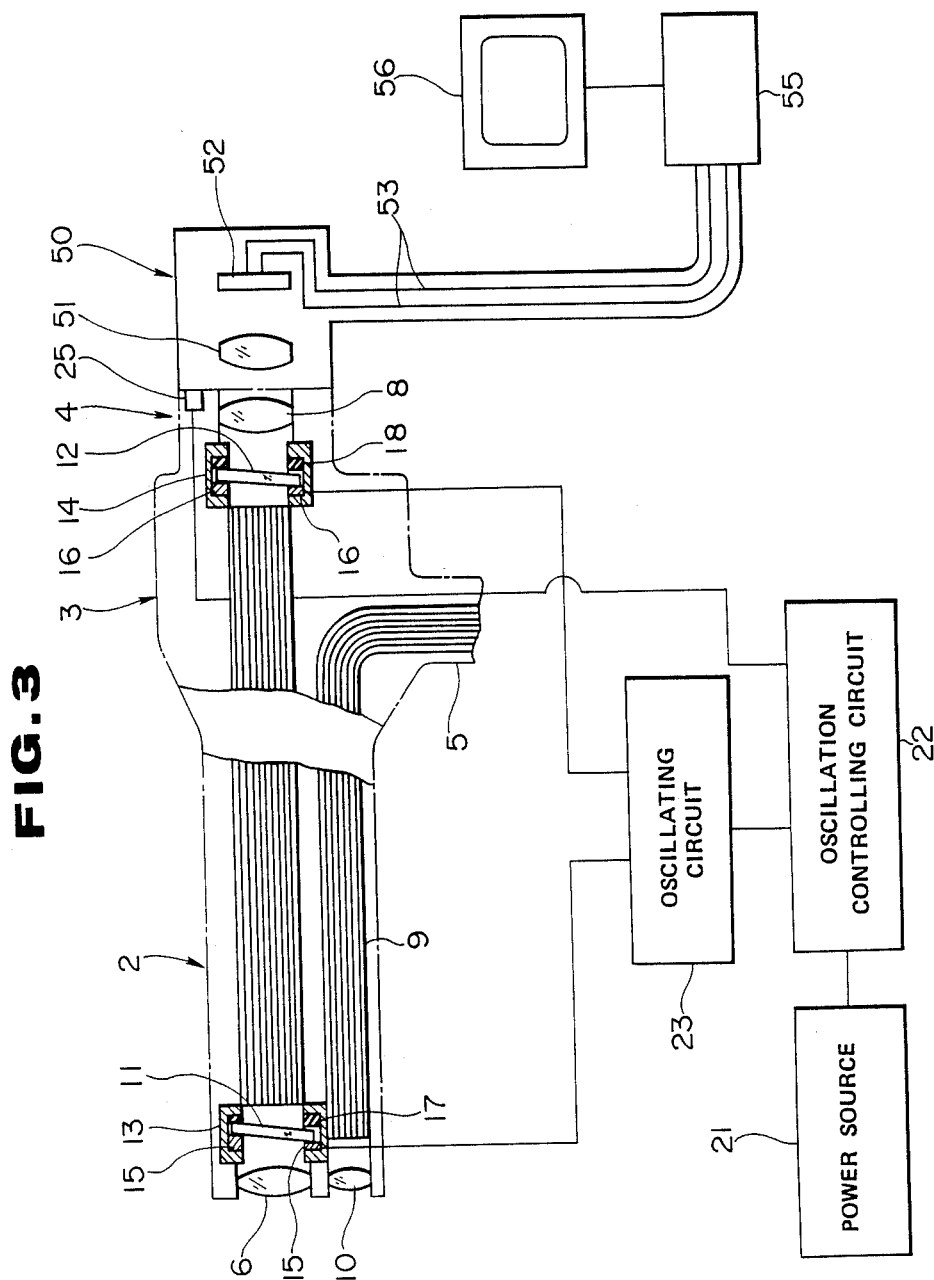
Figure 4:
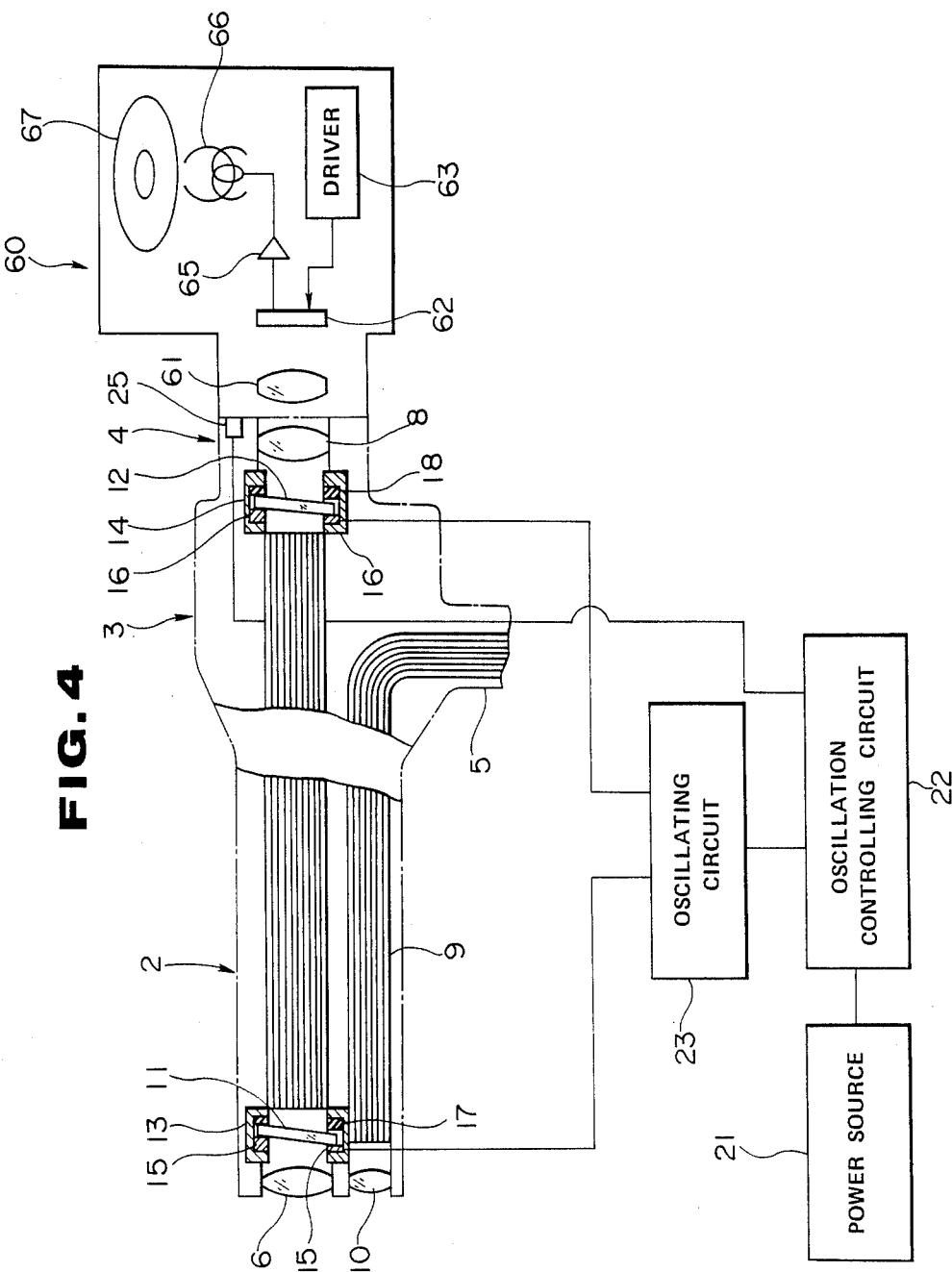
Figure 5:
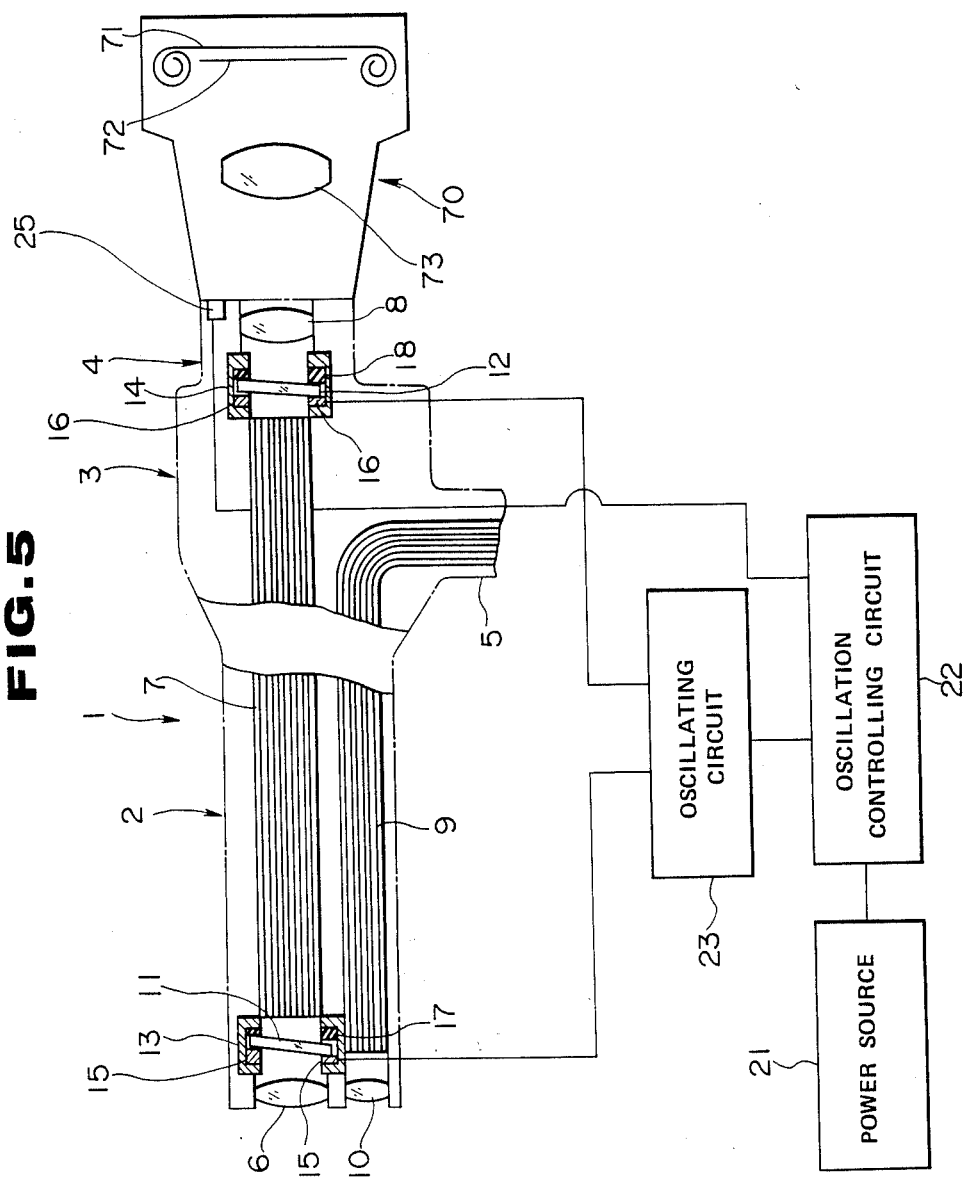

Also, in this embodiment, such image receiving means required to remove moiré fringes as such co-viewing apparatus (called also a lecture scope) 40 as is shown in FIG. 2, such television camera 50 as is shown in FIG. 3 and such electronic still camera 60 as is shown in FIG. 4 can be connected to the eyepiece part 4 of the above mentioned endoscope 1. Also, such image receiving means required to remove mesh patterns as such still camera 70 as is shown in FIG. 5 can be connected.

As shown in FIG. 2, the above mentioned co-viewing apparatus 40 comprises a co-viewing apparatus body 42 having a first eyepiece part 41 in the rear end part, an image guide cable 43 extended out of this co-viewing apparatus body 42 and a second eyepiece part 44 provided in the end part of this image guide cable 43. Within the above mentioned co-viewing apparatus body 41, an image forming lens 45 and beam splitter 46 are arranged in turn on the light path of the beam from the above mentioned eyepiece part 4. An object image having passed through the above mentioned beam splitter 46 is observed from the above mentioned first eyepiece part 41 through an eyepiece lens 47 arranged within this first eyepiece part 41. The front end surface of an image guide 48 consisting of a fiber bundle is arranged in the image forming position of the above mentioned image forming lens 45 in the optical axis extending direction of the beam branched in the vertical direction by the above mentioned beam splitter 46. This image guide 48 is inserted through the above mentioned image guide cable 43 and is extended to the above mentioned second eyepiece part 44 so that the object image formed on the tip surface of the above mentioned image guide 48 may be transmitted to the above mentioned second eyepiece part 44 side by this image guide 48 and may be observed from the above mentioned second eyepiece part 44 through an eyepiece lens 49 arranged within this second eyepiece part 44.

In the case of an observation by using this co-viewing apparatus 40, moiré fringes will be produced on the end surfaces of the image guide 7 of the above mentioned endoscope 1 and the image guide 48 within the above mentioned co-viewing apparatus 40. Therefore, it is desirable to remove these moiré fringes.

As shown in FIG. 3, the above mentioned television camera 50 is provided with an image forming lens 51 and a solid state imaging device 52 arranged in the image forming position of this image forming lens 51. Signal lines 53 are connected to the above mentioned solid state imaging device 52 and are to be connected to a video processor 55 processing the signal of the above mentioned solid state imaging device 52. A monitor 56 is to be connected to the above mentioned video processor 55 so that the object image imaged by the above mentioned solid state imaging device 52 may be displayed in the above mentioned monitor 56.

In the case of imaging an object image by using the television camera 50, moiré fringes will be produced between the pixels of the image guide 7 of the above mentioned endoscope 1 and the pixels of the solid state imaging device 52. Therefore, it is desirable to remove these moiré fringes.

As shown in FIG. 4, the above mentioned electronic still camera 60 is provided with an image forming lens 61 and a solid state imaging device 62 arranged in the image forming position of this image forming lens 61. The above mentioned solid state imaging device 62 is driven by a driver 63. The picture image signal of the still picture image read out of this solid state imaging device 62 is recorded in a floppy disc 67 by a recording head 66 through an amplifier 65. In the case of reproducing the still picture image, with a reproducing apparatus not illustrated, the picture image signal recorded in the above mentioned floppy disc 67 is read out, is processed to be a video signal, is converted to a television signal and is inputted into a monitor to display a still picture image in this monitor.

By the way, the above mentioned electronic still camera 60 may be provided with a mechanical shutter or electronic shutter.

In the case of obtaining a still picture image of an object by using this electronic still camera 60, moiré fringes will be produced between the pixels of the image guide 7 of the above mentioned endoscope 1 and the pixels of the solid state imaging device 62. Therefore, it is desirable to remove these moiré fringes.

As shown in FIG. 5, the above mentioned still camera 70 is provided with a film 71, a shutter 72 arranged on the front surface side of this film 71 and a photographing lens 73 forming on the above mentioned film 71 an image of an object observed with the above mentioned eyepiece part 4.

In the case of photographing the object image with this still camera 70, the still picture will be photographed as magnified. Therefore, it is desirable to remove the mesh patterns made by the fiber bundle forming the image guide 7.

Further, in this embodiment, the eyepiece part 4 of the above mentioned endoscope 1 is provided with a connection sensing apparatus 25 sensing that the above mentioned image receiving means 40, 50, 60 or 70 is connected. This connection sensing apparatus 25 is formed, for example, of an engaging hole and a switch provided in the deep part of this engaging hole. On the other hand, each of the above mentioned image receiving means 40, 50, 60 and 70 is provided with a pin-like switch pressing part which will be engaged in the above mentioned engaging hole and will press the above mentioned switch to be on when the image receiving means is fitted to the eyepiece part 4 of the above mentioned endoscope so that, when any of the above mentioned image receiving means 40, 50, 60 and 70 is connected, the above mentioned switch will be on. Also, each of the above mentioned image receiving means 40, 50, 60 and 70 may be provided with a discriminating signal generating circuit having a resistance or the like connected, for example, between two terminals. On the other hand, the eyepiece part 4 of the above mentioned endoscope 1 may be provided with the connection sensing apparatus 25 sensing the resistance value between two terminals of each of the above mentioned image receiving means 40, 50, 60 and 70 by using a comparator or the like. In such case, when the resistance values of the resistance provided in the respective image receiving means 40, 50, 60 and 70 are made respectively different and any of the resistance values is sensed, it may be sensed that any of the image receiving means 40, 50, 60 and 70 is connected.

The sensing output of the above mentioned connection sensing apparatus 25 is inputted into the above mentioned oscillation controlling circuit 22. This oscillation controlling circuit 22 will make the above mentioned oscillating circuit 23 operative by the above mentioned connection sensing apparatus 25 only when the image receiving means 40, 50, 60 or 70 required to remove moiré fringes or mesh patterns is connected to the eyepiece part 4. That is to say, at the time of the ordinary naked eye observation from the eyepiece part 4, the vibration of the transparent plates 11 and 12 will be stopped.

In this embodiment formed as in the above, when the image receiving means required to remove moiré fringes or mesh patterns, (i.e., the co-viewing apparatus 40, television camera 50, electronic still camera 60 or still camera 70) is connected to the eyepiece part 4 of the endoscope 1, the oscillating circuit 23 will be operative and the transparent plates 11 and 12 arranged in front and rear of the image guide 7 will be vibrated by the same amount of vibration in the same direction as synchronized. By the vibration of these transparent plates 11 and 12, a part of the light path of the observing optical system will be periodically deviated, moiré fringes and mesh patterns by the above mentioned image guide 7 will be removed, the resolution will improve and the information amount will increase.

On the other hand, when the image receiving means required to remove moiré fringes or mesh patterns is not connected to the eyepiece part 4 of the above mentioned endoscope, for example, at the time of an ordinary naked eye observation from the eyepiece part 4, the oscillating circuit 23 will stop and the vibration of the above mentioned transparent plates 11 and 12 will stop. By the way, at the time of the ordinary naked eye observation from the eyepiece part 4, a moving picture will be seen and therefore, even if the mesh patterns are not removed, the apparent resolution will be improved.

Thus, in this embodiment, only when the image receiving means required to remove moiré fringes or mesh patterns is connected to the eyepiece part 4 of the endoscope 1, the transparent plates 11 and 12 will be vibrated. Therefore, as compared with the case of always vibrating the above mentioned transparent plates 11 and 12, the durability is higher and the break, peeling and backlash are harder to cause.

Figure 9:
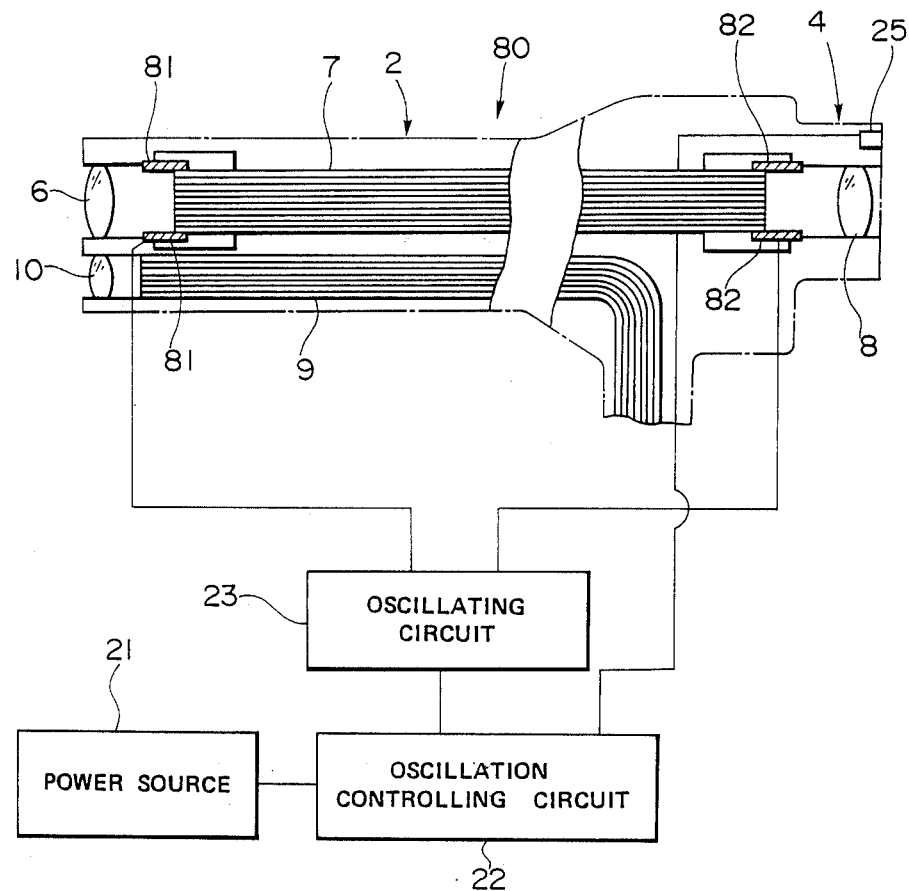
FIG. 9 is an explanatory view showing the formation of an endoscope of the second embodiment of the present invention.

FIG. 9 shows the second embodiment of the present invention.

In the endoscope 81 of this embodiment, the image guide 7 can be rocked in the front end part and rear end part and bimorph vibrators 81 and 82 extended in the axial direction of the image guide 7, fixed each at one end to the endoscope body side and vibrating in the direction intersecting substantially at right angles with the optical axis are connected each at the other end respectively to these front end part and rear end part. The above mentioned bimorph vibrators 81 and 82 are formed each by pasting two voltage elements polarizing in the directions reverse to each other and are fixed, for example, to the vertical and horizontal outer peripheral parts in both end parts of the above mentioned image guide 7 so that those opposed to each other may be synchronously vibrated by the application of an alternating current voltage so as to move the image guide 7 in the end parts in the same direction. Also, the image guide 7 is vibrated in both end parts as synchronized by the same vibration amount.

The above mentioned bimorph vibrators 81 and 82 are driven by the oscillating circuit 23. As in the first embodiment, this oscillating circuit 23 will be operative only when the image receiving means 40, 50, 60 or 70 required to remove moiré fringes or mesh patterns is connected.

In this embodiment, when the image receiving means 40, 50, 60 or 70 required to remove moiré fringes or mesh patters is connected to the eyepiece part 4, the image guide 7 will vibrate in both end parts and the moiré fringes or mesh patterns will be thereby removed. Also, when the bimorph vibrators 81 and 82 are extended in the axial direction of the image guide 7, the diameter of the insertable part 2 will be able to be made as small as possible.

The other formations, operations and effects are the same as in the first embodiment.

By the way, in the first or second embodiment, the objective lens system 6 and eyepiece lens system 8 may be vibrated as synchronized at least partly. The image guide 7 in the eyepiece side end part or the eyepiece lens system 8 only may be vibrated.

The vibrating means may not only vibrate the light path in one or two directions but also rotate and vibrate the light path.

In place of the transparent plates 11 and 12 in the first embodiment, a wedge-like prism may be provided to be vibrated by piezoelectric vibrators 15 and 16 or to be rotated with an ultrasonic motor or the like.

As explained above, according to the first or second embodiment, only when the observing means required to remove moiré fringes or mesh patterns is fitted, at least a part of the observing optical system will be vibrated by a predetermined amount. Therefore, when it is required to remove moiré fringes or mesh patterns, they will be able to be efficiently removed and the durability will improve.

FIGS. 10 to 16 show the third embodiment of the present invention.

In this embodiment, the image guide 7 extended to the eyepiece part 4 through the operating part 3 from the insertable part of an endoscope 111 is vibrated in the eyepiece side end part in the direction intersecting substantially at right angles with the optical axis by a bimorph 115. The bimorph 115 is extended in the optical axis direction and is provided as secured at one end (fixed end) to a fixed member 113a of the eyepiece part 4 and at the other end (free end) to a mouthpiece 7a provided at the eyepiece side end of the image guide 7. A television camera 118 having a photographing lens 116 and solid state imaging device 117 is removably fitted to the eyepiece part 4 so that an image transmitted to the eyepiece side end surface of the image guide 7 may be formed on the solid state imaging device 117 by the photographing lens 116 through the eyepiece lens 8 provided in the eyepiece part 4.

Figure 10:
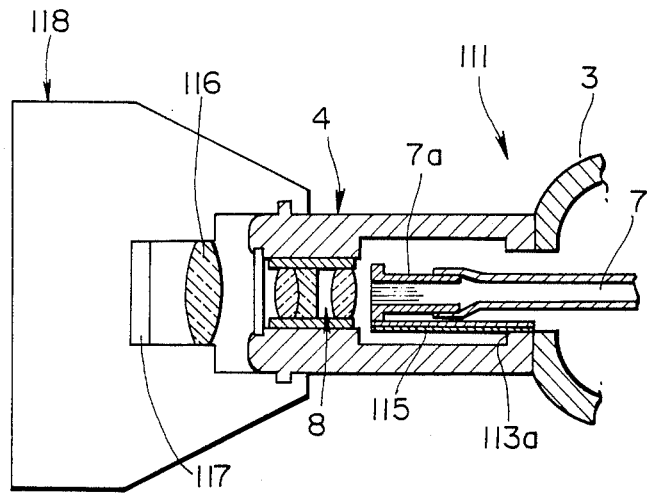
Figure 11:
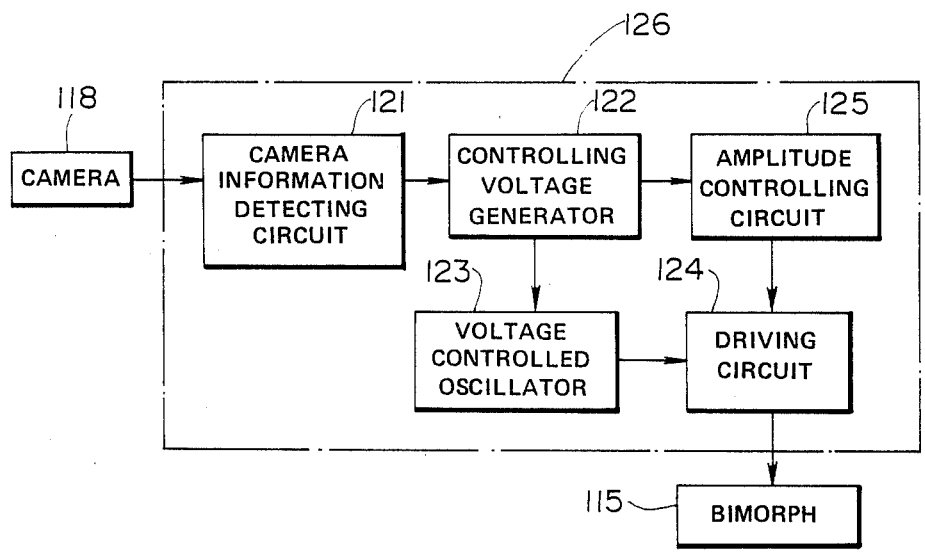

FIG. 11 shows a formation of an example of a control circuit for driving the bimorph 115 shown in FIG. 10. In this embodiment, when the television camera 118 removably fitted to the eyepiece part 4 has various informations, that is, a charge accumulating period of each pixel of the solid state imaging device 117, pixel pitch and color filter array, such information as a repeating pitch of the same color filter will be detected by a camera information detecting circuit 121. Such camera informations are automatically detected by providing a function of transmitting various informations of the television camera 118 in the jointing part, for example, of the television camera 118 with the eyepiece part 4.

In response to the various information of the fitted television camera 118, a required signal corresponding to the television camera 118 is fed to a controlling voltage generator 122 by the camera information detecting circuit 121, thereby a driving signal of a frequency corresponding to the charge accumulating period of each pixel of the solid state imaging device 117 is fed to a driving circuit 124 through a voltage controlled oscillator 123 and the amplitude of the driving signal fed to this driving circuit 124 is controlled through an amplitude controlling circuit 125 in response to the pixel pitch of the solid state imaging device and the repeating pitch of the color filter array to drive the bimorph 115.

By the way, the control circuit 126 having the above mentioned camera information detecting circuit 121, controlling voltage generator 122, voltage controlled oscillator 123, driving circuit 124 and amplitude controlling circuit 125 is provided in the light source apparatus to which the operating part 3 of the endoscope 111 and the entrance end of the light guide of the endoscope 111 are connected but, among them, the driving circuit 124 is provided preferably near the bimorph 115 in order to prevent the attenuation and the like of the signal. In this embodiment, the image guide 7 is vibrated likewise in the objective side end part in the direction intersecting substantially at right angles with the optical axis as synchronized with the eyepiece side end part.

Figure 12:
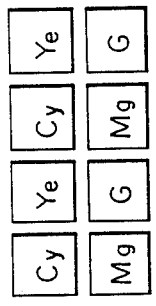
Figure 13:
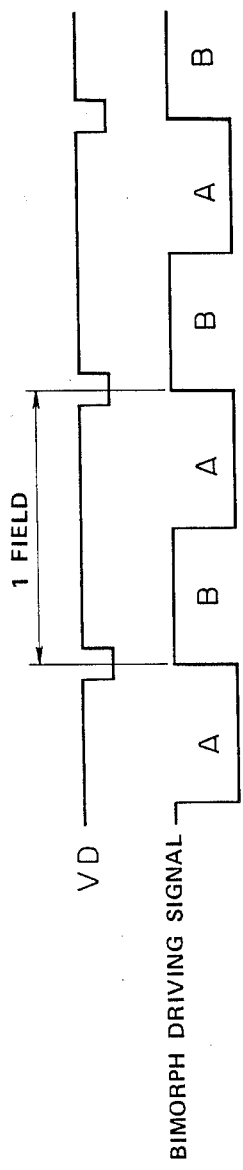
Figure 14:
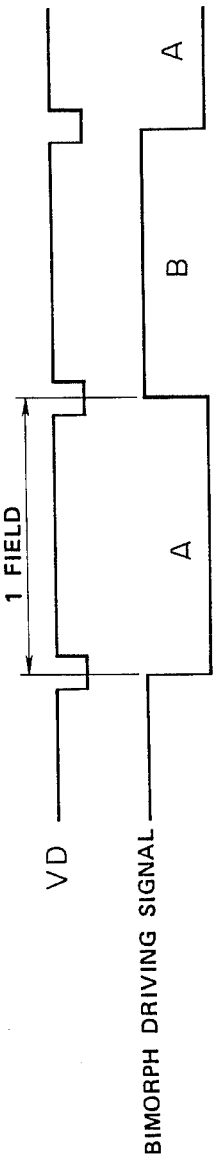
Figure 17:
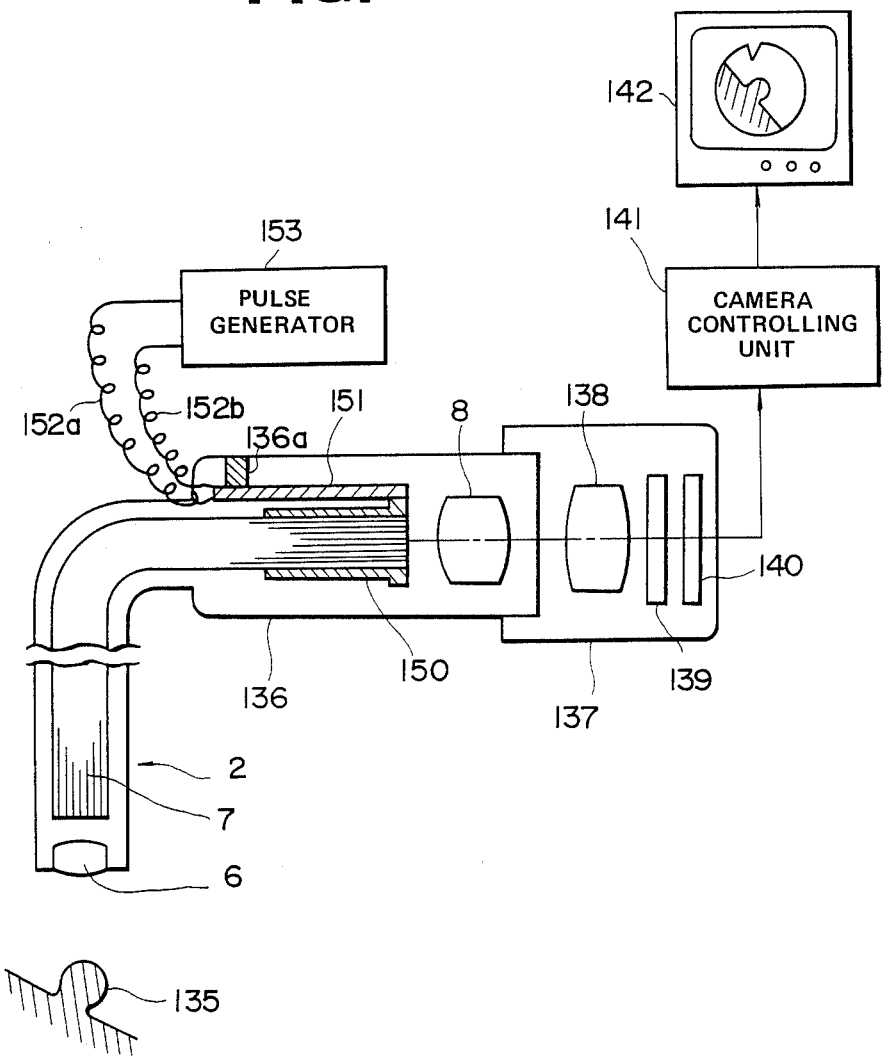
FIGS. 17 to 21 relate to the fourth embodiment of the present invention.

The operation of this embodiment is explained as follows. In the case where the television camera 118 is a black-and-white monochromatic camera or in the case where it is a color camera and color filters of two colors are alternately arranged in response to the respective pixels in the horizontal direction in the color filter array as shown in FIG. 12, the image guide 7 will be vibrated at a frequency corresponding to the signal accumulating period of each pixel by making the amplitude of the vibration of the image guide 7 one pitch (one pixel) of the arrangement of pixels. In other words, in the case of a field accumulating mode, as shown in FIG. 13, the arrangement will be moved by one pixel in the period of one field as synchronized with a vertical synchronous signal VD of the solid state imaging device 117. In other words, one field will be one period of the vibration. Therefore, the vibrating frequency in this case will be 60 Hz in the NTSC system. In the case of a frame accumulating mode, as shown in FIG. 14, the arrangement will be moved by one pixel with 2 fields. That is to say, 2 fields will be one period of the vibration. Therefore, the vibrating frequency in this case will be 30 Hz.

Thus, fibers 102a and 102b corresponding to a pixel 101a as shown in FIG. 15(A) in a period A in which the bimorph driving signal shown in FIGS. 13 and 14 is in the first state will correspond to an adjacent pixel 101b as shown in FIG. 15(B) in a period B in which the bimorph driving signal is in the next second state and the other fibers adjacent to the fibers 102a and 102b will correspond to the pixel 101a. Therefore, the information of the adjacent pixel will mix in each pixel, therefore false signals will be reduced and the generation of moiré fringes will be able to be effectively prevented.

In case color filters R, G and B of three colors are repeatedly arranged in response to the respective pixels in the horizontal direction in the color filter array as shown in FIG. 16, the generation of moiré fringes are similarly prevented when the image guide is vibrated at an amplitude of ⅓ the repeating pitch of each color filter. That is to say, the amplitude of the vibration will be one pixel part in the black-and-white case and will be ⅓ the repeating pitch of the same color filter in the color filter array in the color case.

By the way, in the above described embodiment, the camera information is automatically detected with the television camera 118 fitted to the eyepiece part 4 of the endoscope 111 but may be manually input. In the frame accumulating mode, the image guide is vibrated by one cycle in two fields as shown in FIG. 14 but may be vibrated by one cycle in one field as in FIG. 13. Further, the image guide 7 may be vibrated only in the eyepiece side end part. The driving means is not limited to the bimorph but also such various things as a piezoelectric oscillator, electromagnet and ultrasonic vibration adder can be used.

As described above, according to this embodiment, the generation of moiré fringes can be effectively prevented by a simple cheap formation whereby the image guide is vibrated in the eyepiece side end part in the direction intersecting substantially at right angles with the optical axis with a driving signal of a frequency corresponding to the charge accumulating period of each pixel of the solid state imaging device without using a quartz filter or pressing the picture image.

FIGS. 17 to 21 show the fourth embodiment of the present invention.

The image guide 7 is extended through the insertable part 2. On the other hand, a light guide leading an illuminating light, forceps channel and air and water feeding channel are also provided but are not shown in the drawings. An image of an observed object 135 is formed on the entrance end surface of the image guide 7 by the objective leans system 6 and is led to the exit end surface within an observing part 136 through the image guide 7. A bimorph 151 is connected at one end to the tip of a mouthpiece 150 provided in the eyepiece side end part of the image guide 7 and is connected at the other end to a fixing member 136a forming the observing part 136. The electrode of the bimorph 151 is connected to a pulse generator 153 through lead wires 152a and 152b. Therefore, when a voltage is applied to the bimorph 151 from the pulse generator 153, the image guide 7 will vibrate in the eyepiece side end part in the vertical direction in FIG. 17. The light emitted from the eyepiece side end surface of the image guide 7 is received by a solid state imaging device 140 consisting of a CCD through the eyepiece lens system 8, a photographing lens 138 of a television camera unit 137 removably fitted to the observing part 136 as an adapter and a low pass filter 139 consisting of a quartz plate. The output signal of this solid state imaging device 140 is processed with a camera controlling unit 141 to make a television signal which is fed to a monitor 142 to diaplay the image of the observed object 135.

Figure 18:
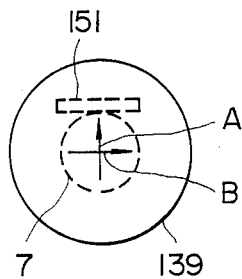

When a driving signal of a frequency considerably higher than the field frequency of the television signal is applied to the bimorph 151, the image guide 7 will vibrate in the eyepiece side end part vertically in the direction indicated by the arrow A in FIG. 18.

Figure 20:
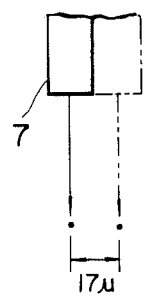
Figure 21:
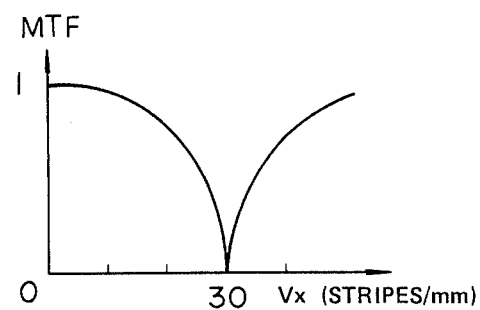

In such endoscope apparatus, when, for example, the image guide 7 is vibrated in the eyepiece side end part in the x direction at a frequency well higher than the field frequency of the television with an amplitude of 17 μm. as shown in FIG. 20, the same response characteristic as of the low pass filter will be obtained as shown in FIG.

21 and therefore the generation of moiré fringes will be able to be controlled.

Therefore, in FIG. 18, when the vibrating direction of the image guide 7 is made to intersect, for example, at right angles with the double refracting direction B of the low pass filter 139 consisting of a quartz plate, the moiré fringe components in the directions A and B can be erased. By the way, the vibrating direction A need not be made to always intersect at right angles with the double refracting direction B but may be the direction of the least moiré fringes.

Figure 19:
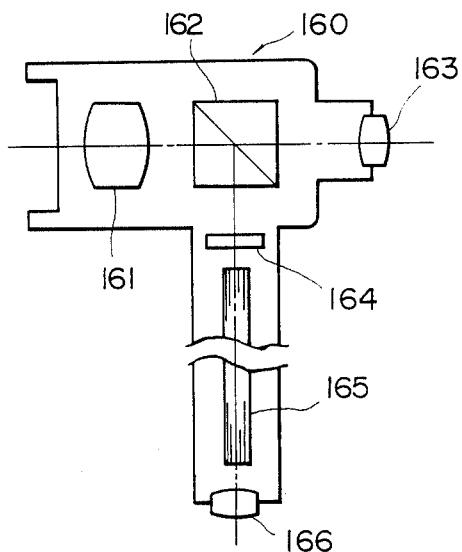
Figure 33:
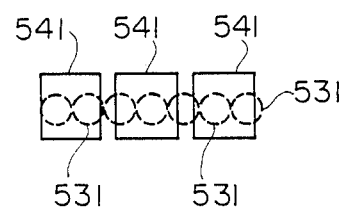
FIG. 33 is an explanatory view showing the relative relations between pixels of a solid state imaging device and fibers.
Figure 34:
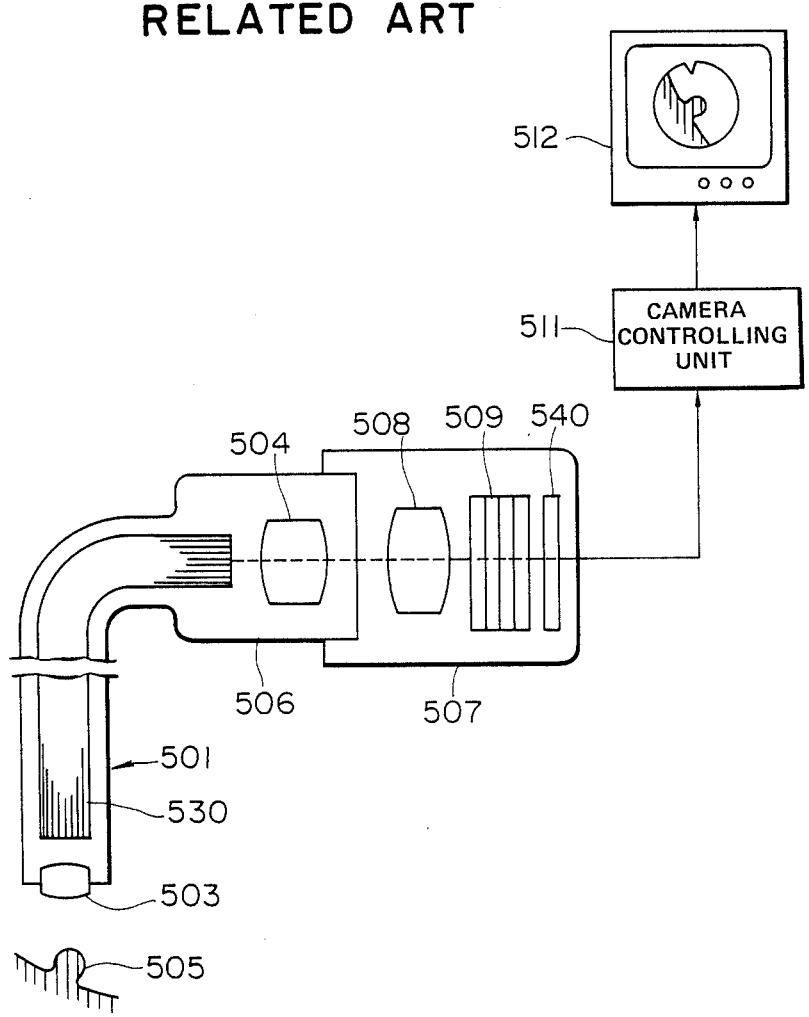
FIG. 34 is an explanatory view showing the structure of an endoscope system of a related art example.
Figure 35:
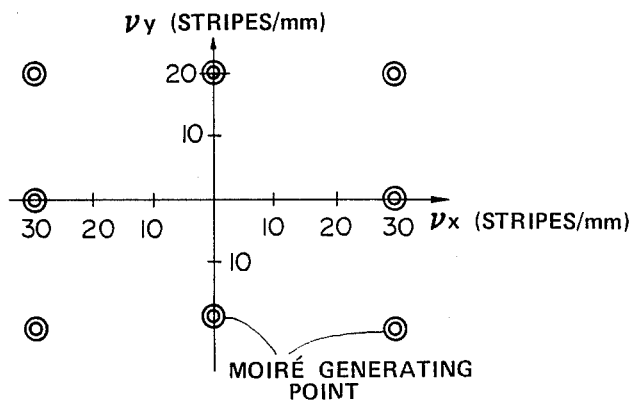
FIG. 35 is an explanatory view showing the generation of moiré fringes in an endoscope system of a related art example.
Figure 36:
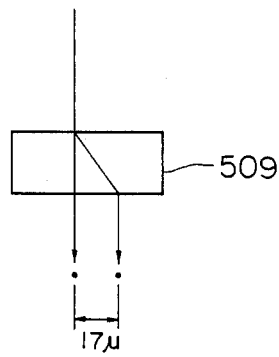
FIG. 36 is an explanatory view showing double refractions of a low pass filter made of a quartz plate.
Figure 37:
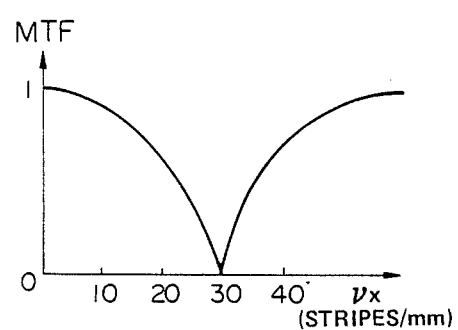
FIG. 37 is an explanatory view showing a response characteristic of a low pass filter made of a quartz plate.

In this embodiment, as the television camera unit 137 can be fitted as an attachment to the observing part 136, the television camera unit may be removed and such lecture scope 160 as is shown in FIG. 19 may be fitted. Such lecture scope 160 is provided with a relay lens 161, light path dividing prism 162, first eyepiece lens 163, low pass filter 164, image guide 165 and second eyepiece lens 166 so that two persons can simultaneously observe. In this case, if observed through the image guide 165, as the fiber bundle of the image guide 165 also has fixed patterns, such moiré fringes as are described above will be likely to be generated. However, when the image guide 7 is vibrated in the eyepiece side end part as described above and the low pass filter 164 erasing moiré fringes in the direction different from this vibrating direction is provided, moiré fringes will be able to be effectively removed. In the endoscope apparatus of the related art example shown in FIG. 33, as the low pass filter 509 is contained in the television camera unit 137, in case the television camera unit 137 is removed and the lecture scope 160 is fitted, moiré fringes will not be removed.

By the way, in the above described embodiment, one low pass filter 139 is inserted between the photographing lens 138 and solid state imaging device 140 but, in case moiré fringes can not be well erased by merely vibrating the image guide 7 in the eyepiece side end part in one direction only, two or more low pass filters may be arranged. In the above described embodiment, the image guide 7 is vibrated but the eyepiece lens 8 or photographing lens 138 may be vibrated. Also, in the above described embodiment, the bimorph which is a piezoelectric driving apparatus is used as a driving means vibrating the image guide but another piezoelectric driving apparatus or electromagnetic driving apparatus may be used. Further, in the above described embodiment, the imaging apparatus can be removably fitted as an attachment to the observing part but may be formed integrally with the observing part.

Figure 22:
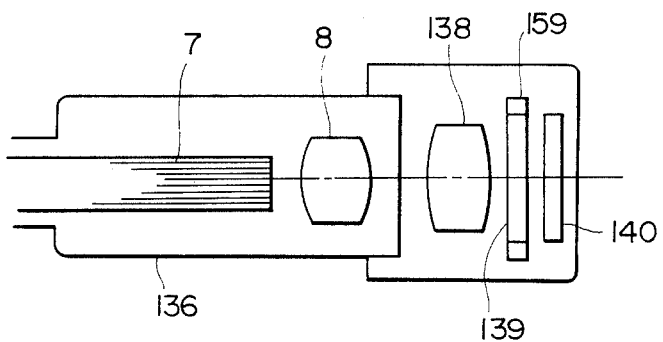
FIG. 22 is an explanatory view showing a television camera unit in the fifth embodiment of the present invention.

FIG. 22 shows the fifth embodiment of the present invention. In this embodiment, the image guide 7 is not vibrated but the low pass filter 139 is rotated reciprocally or in one direction with the optical axis as a center, for example, by an ultrasonic motor 159. The formation of the above mentioned ultrasonic motor shall be explained in the ninth embodiment.

Thus, by rotating the low pass filter 139, moiré fringe components in different directions can be erased with one low pass filter 139.

The other formations, operations and effects are the same as in the fourth embodiment.

As described above, by vibrating the image guide in the eyepiece side end part or the imaging optical system in the direction different from the moiré fringe erasing direction of the low pass filter or by rotating the low pass filter, the generation of moiré fringes can be effectively controlled with less low pass filters and the television camera unit can be made smaller, lighter and cheaper.

Figure 23:
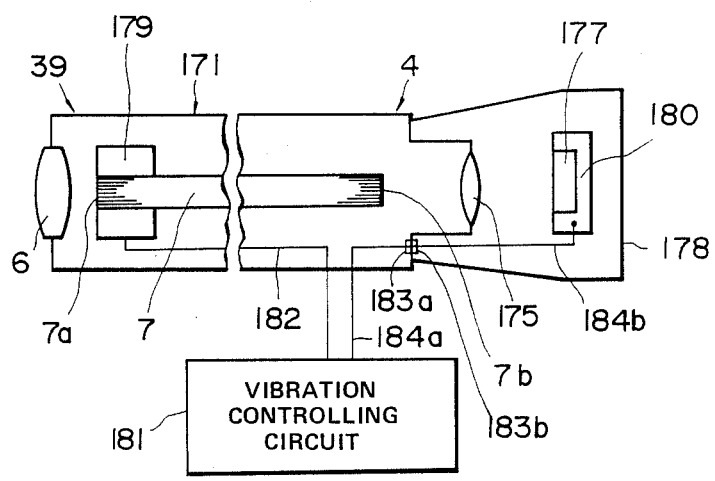
FIG. 23 is an explanatory view showing the formation of an endoscope system of the sixth embodiment of the present invention.

FIG. 23 shows the sixth embodiment of the present invention.

An endoscope 171 has an objective lens system 6 provided in the tip part 39 of its insertable part, en eyepiece and photographing lens 175 provided in the eyepiece part 4 and an image guide 7 consisting of a fiber bundle extended over the eyepiece part 4 from the tip part 39 so that an image of an observed object may be formed on the object side end surface 7a of the image guide 7, the image transmitted to the eyepiece side end surface 7b of this image guide 7 may be observed with a naked eye through the eyepiece and photographing lens 175, a television camera 178 having a solid state imaging device 177 may be removably fitted to the eyepiece part 4 and thereby the image formed on the solid state imaging device 177 through the objective lens system 6, image guide 7 and eyepiece and photographing lens 175 may be displayed on a monitor.

In this embodiment, the image guide 7 in the objective side end part and the solid state imaging device 177 are displaceably supported respectively through a first and second driving means 179 and 180 consisting of such piezoelectric vibrators as, for example, bimorphs, these first and second driving means 179 and 180 are driven by a vibration controlling circuit 181, the image guide 7 in the objective side end part and the solid state imaging device 177 are vibrated as synchronized in the direction intersecting substantially at right angles with the optical axis at an amplitude of one pitch (one pixel) of the arrangement of the light receiving elements, for example, of the solid state imaging device 177. By the way, the first driving means 179 is directly connected to the vibration controlling circuit 181 through a lead wire 182. As the television camera 178 is removably fitted to the eyepiece part 4, contacts 183a and 183b are provided respectively in their jointing parts. The second driving means 180 is connected to the vibration controlling circuit 181 through these contacts 183a and 183b and lead wires 184a and 184b.

According to this embodiment, as the solid state imaging device 177 is vibrated in the direction intersecting substantially at right angles with the optical axis with respect to the eyepiece side end surface 7b of the image guide 7, the picture image information of the adjacent light receiving element will be mixed into each light receiving element of the solid state imaging device 177. Therefore, the regularity of the fibers of the image guide 7 and the regularity of the light receiving elements of the solid state imaging device will be relieved, the generation of moiré fringes can be effectively prevented and the meshes by the clothing through which the light is not transmitted by the fibers can be effectively removed. Further, as the image guide 7 is vibrated also in the objective side end part in the same direction as synchronized with the vibration of the solid state imaging device 177, the resolution will not reduce.

By the way, in the above described embodiment, the image guide 7 is vibrated in the objective side end part by the first driving means 179 but, instead of it, at least a part of lenses of the objective lens system 6 may be vibrated or parallel plane plates provided within the objective lens system 6 may be vibrated by the first driving means so that the image formed on the objective side end surface 7a of the image guide 7 may be vibrated in the direction intersecting substantially at right angles with the optical axis.

As described above, according to this embodiment, without using a crystal filter or processing a picture image, the image formed on the end surface of the image guide by the objective lens system and the solid state imaging device imaging this image through the image guide are vibrated as synchronized in the direction intersecting substantially at right angles with the optical axis and therefore the generation of moiré fringes can be effectively prevented with a simple and cheap formation without reducing the resolution.

Figure 24:
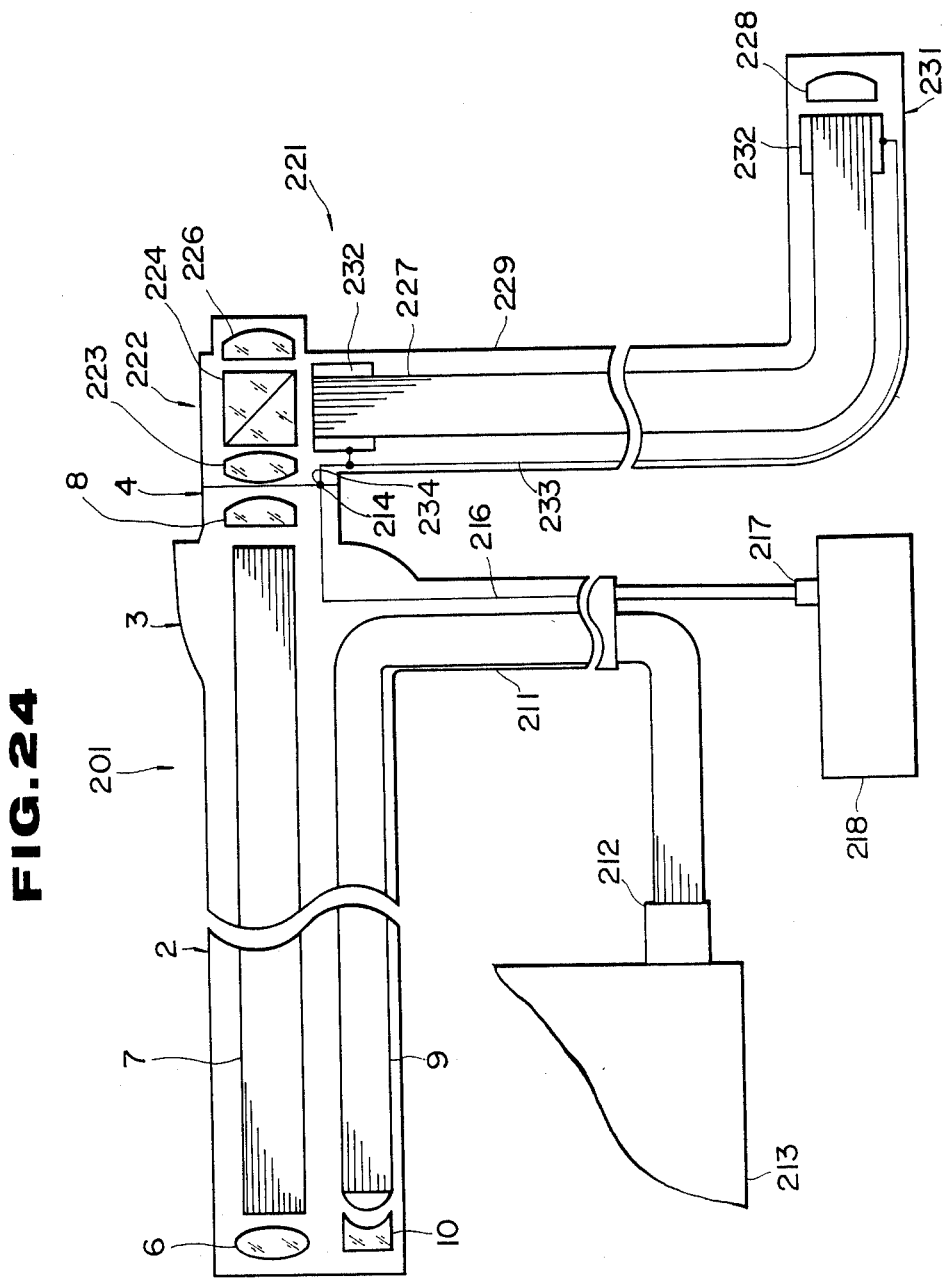
FIG. 24 is an explanatory view showing the formation of an endoscope system of a seventh embodiment of the present invention.

FIG. 24 shows the seventh embodiment of the present invention.

As shown in FIG. 24, an endoscope 201 is provided with an elongate insertable part 2, an operating part 3 connected to the rear of the insertable part 2 and an eyepiece part 4 connected to the rear of this operating part 3. An image guide 7 made by bundling many fine optical fibers is contained within the endoscope 201 and is provided on the tip side of the insertable part 2 to be the objective side with an objective lens system 6 and on the rear end side of the eyepiece part 4 with an eyepiece lens 8.

Further, within the endoscope 201, a light distributing lens 10 is provided at the tip and a light guide 9 is provided in parallel with the image guide 7 on the rear end side of this light distributing lens 10, is inserted through a universal cord 211 extended from the side part of the above mentioned operating part 3 and is connected to a light source apparatus 213 through a connector 212 provided at the end. Further, within the above mentioned universal cord 211, a signal line 216 having a contact 214 on the rear end connecting surface of the eyepiece part 4 is connected through a connector 217 to a vibration controlling part 218 generating a driving signal.

A first eyepiece part 222 of an endoscope co-viewing apparatus 221 is connected at one end to the above mentioned eyepiece part 4. An image forming lens 223, a beam splitter passing a part of an entering light in the optical axis direction and reflecting a part of the entering light in the direction vertical to the optical axis direction and an eyepiece lens 226 are arranged with the optical axes made to coincide within this first eyepiece part 222.

A co-viewing image guide 227 and a flexible tube 229 containing an eyepiece lens 228 in the rear of the exit end side are extended from the side part of the above mentioned first eyepiece part 222. A second eyepiece part 231 is formed in the end part to be the eyepiece side of this flexible tube 229. Piezoelectric elements 232 are fitted respectively to the side parts adjacent to the entrance end and exit end of the co-viewing image guide 227 and are connected to a signal line 233 connected to a contact 234 provided on the co-viewing apparatus 221 side connecting surface connected with the endoscope 201 eyepiece part 4 connecting surface. This contact 234 is connected with the contact 214 on the endoscope 201 side. Further, the above mentioned piezoelectric elements 232 are connected to the above mentioned vibration controlling part 218 through the contacts 214 and 234. By the driving signal generated by this vibration controlling part 218, the arrangement of the optical fibers of the co-viewing image guide 227 on the co-viewing apparatus 221 side is vibrated with such amplitude as produces, for example, ½ pitch deviation in the direction vertical to the arrangement of the optical fibers of the observing image guide 7 and to the optical axis.

With the above-discussed structural arrangement, the light emitted from the light source apparatus 213 and radiated to an object from the light distributing lens 10 through the light guide 9 will be reflected by the object and this reflected light will be made to form an optical image at the entrance end of the observing image guide 7 by the objective lens system 6. The above mentioned optical image will be transmitted by the observing image guide 7 to the eyepiece lens 226 side on the endoscope co-viewing apparatus 221 side, will be partly reflected vertically to the optical axis by the beam splitter 224 and will be transmitted to the eyepiece lens 228 through the co-viewing image guide 227.

Now, the piezoelectric elements 232 fitted respectively to the entrance end and exit end of the co-viewing image guide 227 on the co-viewing apparatus 221 side will be vibrated by the driving signal generated from the vibration controlling part 218 and obtained through the endoscope 201 so that the arrangement of the optical fibers forming the co-viewing image guide 227 may be deviated, for example, by ½ pitch with respect to the arrangement of the optical fibers forming the observing image guide 7 to prevent the generation of moiré fringes and meshes in the optical image obtained on the eyepiece lens 228 side.

As in the above, according to this embodiment, moiré fringes can be prevented and therefore an image high in the resolution can be obtained.

Figure 25:
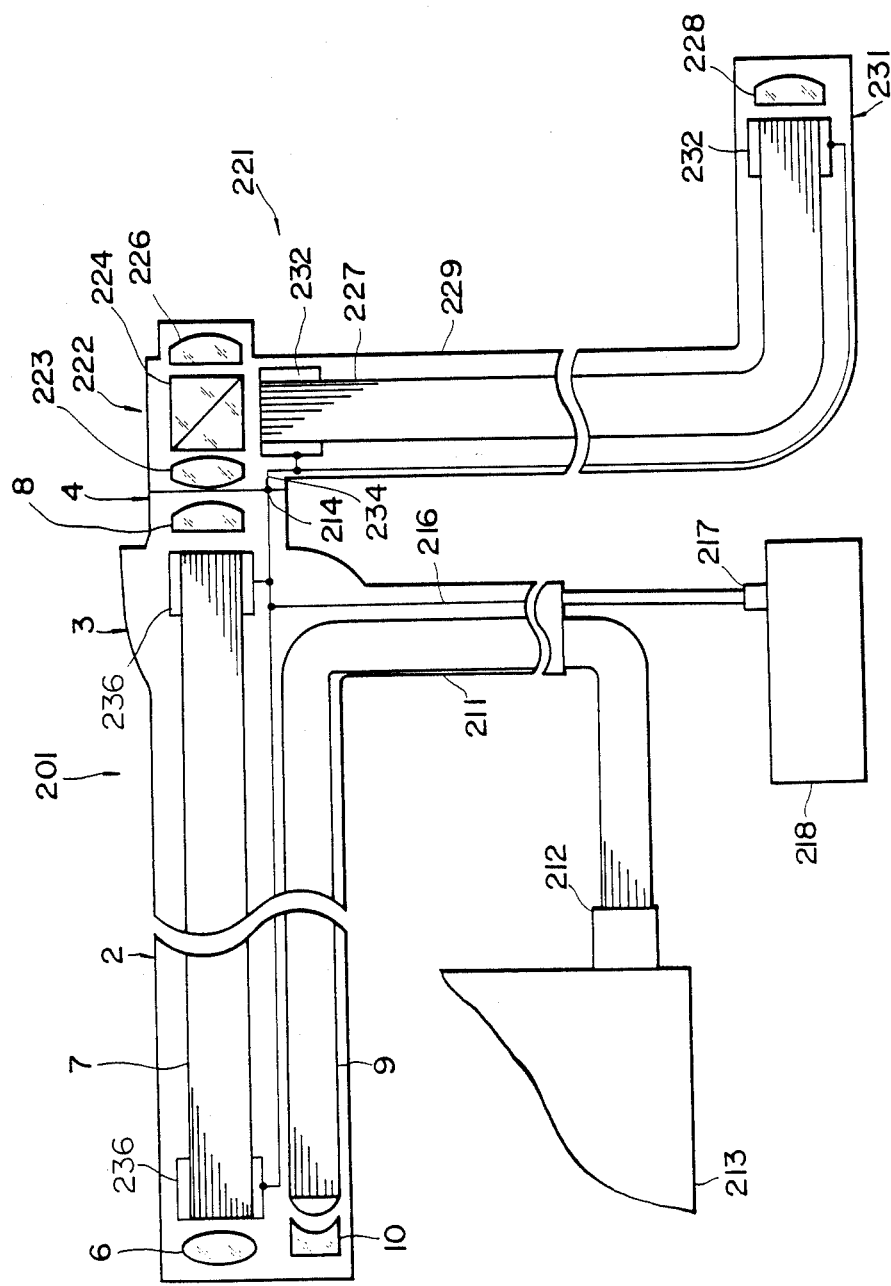
FIG. 25 is an explanatory view showing the formation of an endoscope system of an eighth embodiment of the present invention.

FIG. 25 shows the eighth embodiment of the present invention.

In this embodiment, piezoelectric elements 236 synchronously vibrated by the driving signal received from the vibration controlling part 218 are fitted respectively to the sides adjacent to the entrance end and exit end of the observing image guide 7 also in the endoscope 201 of the seventh embodiment so that the observing image guide 7 and co-viewing image guide 227 may be synchronously vibrated.

Therefore, a high resolution image having no generation of moiré fringes and meshes can be obtained in the second eyepiece part 231 of the co-viewing apparatus 221 and photographed by the still camera connected to the second eyepiece part 231.

The other formations, operations and effects are the same as in the seventh embodiment.

As explained above, according to the seventh and eighth embodiment, the co-viewing image guide is vibrated so that the arrangement of the co-viewing image guide may be deviated, for example, by ½ pitch with respect to the arrangement of the observing image guide to be able to prevent the generation of moiré fringes and meshes and obtain an image of a high resolution.

Figure 26:
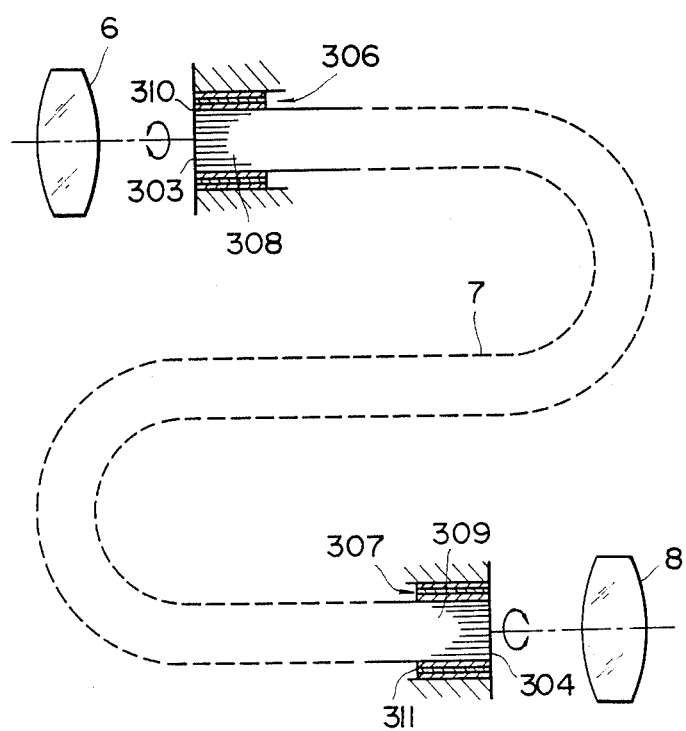
FIGS. 26 and 27 relate to the ninth embodiment of the present invention.
Figure 27:
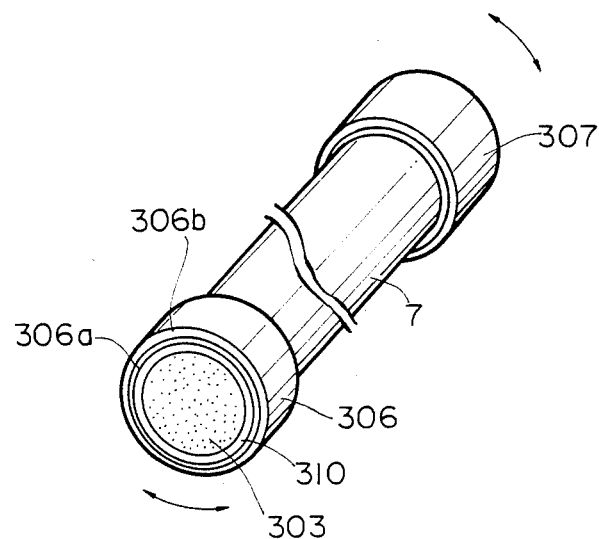

FIGS. 26 and 27 show the ninth embodiment of the present invention.

In this embodiment, the same as in the second embodiment, an ultrasonic motor is used as a driving means in driving the image guide 7 in each end part.

FIG. 26 is a schematic view of an observed image transmitting system having the image guide 7. The observed image applied to the objective side image guide end surface 303 is led to the eyepiece side through fiber elements to appear on the eyepiece side image guide end surface 304 and is observed through the eyepiece side optical system 8. Ultrasonic motors 306 and 307 are provided respectively in the end parts of the image guide 7 to rotate the image guide in the end parts 308 and 309 in the outer peripheral direction to remove moiré fringes or meshes.

By the way, the ultrasonic motor is rotated by the friction force between a vibrator fitted with piezoelectric ceramics to generate a flexing vibration and a mover strongly pressed by the vibrator. A linear motion may be made but, in this embodiment, a motor making a rotary motion is used.

As shown in FIG. 27, in this embodiment, the ultrasonic motors 306 and 307 are provided respectively along mouthpieces 310 and 311 provided respectively on the outer peripheries of the objective side end part and eyepiece side end part of the image guide 7. The ultrasonic motor has a stator (vibrator) and rotor (mover). The objective side ultrasonic motor 306 shall be explained. A motor 306a secured to the mouthpiece 310 is pressed against a stator 306b. When a voltage is applied, the stator will be flexed to cause fixed waves. When the fixed waves deviated in the position and phase are synthesized to be converted to proceeding waves, the rotor 306a will be rotated. In this case, it is needless to say that the stator 306b is fixed to each of the tip rigid part body and eyepiece rigid part body. When twisting rotations, that is, reciprocating rotations of a minute angle are given as synchronized in the same direction on both of the objective side and eyepiece side, the meshes of the image guide 1 will be able to be effectively removed. If the image guide 7 is comparatively short and is comparatively small in flexibility over the entire length, instead of the twisting rotarious, rotations in the same direction may be made.

The other formations, operations and effects are the same as in the second embodiment.

Figure 28:
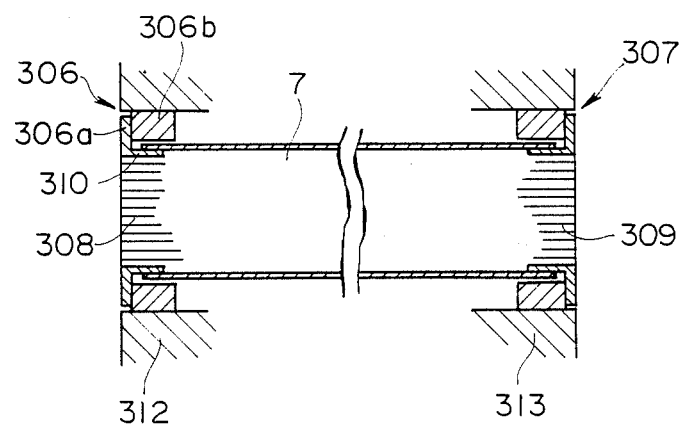
FIG. 28 is a sectioned view showing ultrasonic motors and an image guide in a 10th embodiment of the present invention.

FIG. 28 shows the tenth embodiment of the present invention. The same reference numerals are attached respectively to the parts corresponding to those of the ninth embodiment. In this embodiment, the flange of a mouthpiece provided in each end part of the image guide 7 is operated as a rotor. The objective side ultrasonic motor 306 shall be explained. The flange of the mouthpiece 310 is strongly pressed against the stator 306b fixed to the tip rigid part 312 so as to operate as a rotor 306a. The stator of an ultrasonic motor 307 is fixed also to the eyepiece side forming part 313 so that, when both ultrasonic motors 306 and 307 are driven, the image guide in the end parts 308 and 309 may be reciprocally rotated by a minute angle or rotated the same as in the ninth embodiment.

Figure 29:
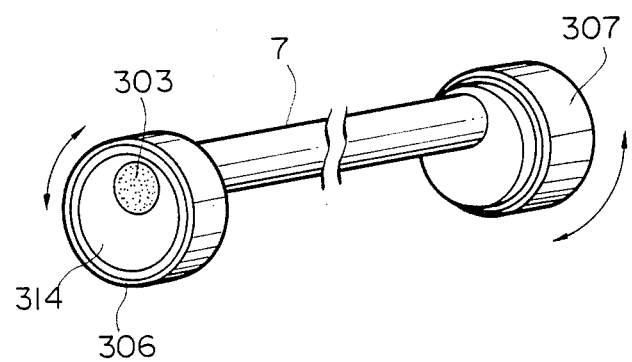
FIG. 29 is a perspective view showing ultrasonic motors and an image guide in an 11th embodiment of the present invention.

FIG. 29 shows the 11th embodiment of the present invention which is a modification of the ninth embodiment. The center of the image guide 7 is deviated to be eccentric from the center of a mouthpiece 314. In the formation of the ultrasonic motors 306 and 307, the drive is the same as in the case of the ninth embodiment but the mouthpiece 314 will rotate with the rotation of the rotor to effectively remove the meshes of the entire image guide 7. That is to say, in the case of the ninth embodiment, the vibration amount will be taken to be larger on the outer periphery of the image guide 7 but to be substantially nil near the center to hardly remove meshes. In this respect, in the 11th embodiment, the vibration amount will be taken to be substantially uniform over the entire image guide 7 to be able to uniformly remove meshes. By the way, in this embodiment, a dead space of the mouthpiece 314 will be produced but, if a hole is made here and another member is incorporated into the hole, there will be no problem in utilizing the space.

Figure 30:
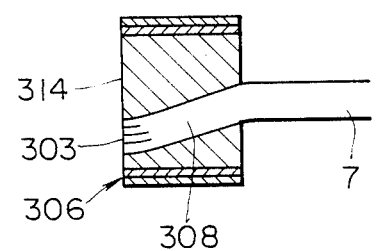
FIG. 30 is a sectioned view showing the vicinity of the end aprt of an image guide in a 12th embodiment of the present invention.
Figure 31:
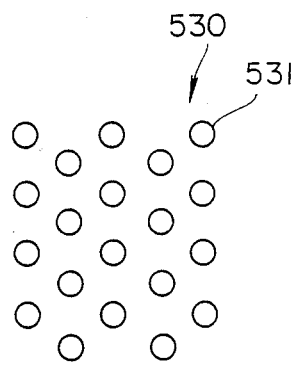
FIG. 31 is an explanatory view showing the arrangement of optical fibers of an image guide.
Figure 32:
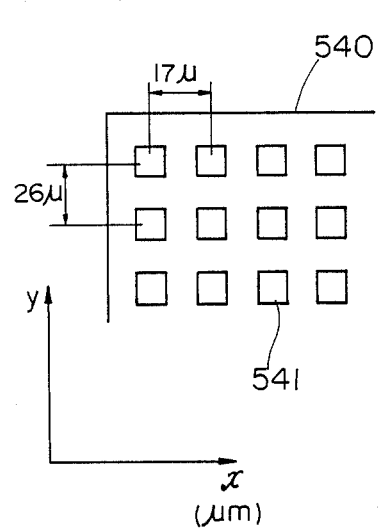
FIG. 32 is an explanatory view showing the arrangement of pixels of a solid state imaging device.

FIG. 30 shows the 12th embodiment of the present invention which is a modification of the 11th embodiment. The image guide 7 is provided as bent in the end part 308 so that the center may be eccentric within the mouthpiece 34 but coincide with the rotary axis of the ultrasonic motor 306 in the part extended out of the mouthpiece 314. Thereby, while the same effect as in the 11th embodiment is produced in removing meshes, the movement of the extended part of the image guide 7 can be made smaller, therefore the movement in the curvable part can be made smaller and such damage as the break of the image guide 7 can be prevented.

As in the above, according to the 9th to 12th embodiments, there can be provided an endoscope system wherein an ultrasonic motor is provided on the outer periphery of the end part of an image guide so as to reciprocally rotate by a minute angle or rotate on the image guide end part, therefore moiré fringes or meshes can be removed and the resolving power can be improved.

In this invention, it is apparent that working modes different in a wide range can be formed on the basis of this invention without deviating from the spirit and scope of the invention. This invention is not restricted by its specific working mode except being limited by the appended claims.

What is claimed is:

1. An endoscope system, comprising:
    an endoscope having an elongated insertable member, an objective optical system provided in a tip portion of said insertable member, an eyepiece member provided on a rear end portion of said insertable member and an image transmitting means having a fiber bundle for transmitting to said eyepiece member an image formed by said objective optical system;
    an image receiving means including a plurality of pixels arranged at a predetermined pattern operable connected to said eyepiece member of said endoscope having an image receiving portion on which the image transmitted by said image transmitting means is formed through said eyepiece member; and
    a vibrating means for relatively vibrating said image receiving portion and said image formed on said image receiving portion to thereby prevent generation of moiré caused by a fiber arrangement of said fiber bundle and by said plurality of pixels of said image receiving portion.

2. An endoscope system according to claim 1, wherein said vibrating means relatively vibrates in the direction intersecting substantially at right angles with an optical axis said image formed on said image receiving portion and said image receiving portion.

3. An endoscope system according to claim 1, wherein said image receiving means is a television camera having a solid state imaging device as an imaging means and said image receiving portion is an image receiving surface of said solid state imaging device.

4. An endoscope system according to claim 1, wherein said image receiving means is a co-viewing apparatus having a beam separating means for separating the light from the eyepiece part of said endoscope into a plurality of beams, a plurality of eyepiece members to which the respective beams, separated by said beam separating means, are led and a second image transmitting means having a fiber bundle for transmitting at least one beam separated by said beam separating means to the corresponding eyepiece part and said image receiving part is an image receiving side end surface of said second image transmitting means.

5. An endoscope system according to claim 1, wherein said image receiving means is an electronic still camera having a solid state imaging device as an imaging means and a recording means for recording a still picture image imaged by said solid state imaging device and said image receiving part is an image receiving surface of said solid state imaging device.

6. An endoscope system according to claim 1, further comprising a means for relatively synchronizing an objective side end surface of said transmitting means and an image formed on said end surface with the relative vibration of said image receiving portion and the image formed thereon which are vibrated with the same amount of vibration.

7. An endoscope system according to claim 1, wherein said vibrating means has a transparent plate provided between said eyepiece side end surface of said image transmitting means and said image receiving portion and a driving means for vibrating said transparent plate so that light having passed through said transparent plate vibrates in the direction intersecting substantially at right angles with an optical axis.

8. An endoscope system according to claim 7 wherein said driving means has a piezoelectric member.

9. An endoscope system according to claim 1, wherein said vibrating means has a driving means for vibrating said image transmitting means in an eyepiece side portion in the direction intersecting substantially at right angles with an optical axis.

10. An endoscope system according to claim 9, wherein said driving means has a piezoelectric member.

11. An endoscope system according to claim 10, wherein said piezoelectric element is provided in the axial direction of said image transmitting means.

12. An endoscope system according to claim 10, wherein said driving means has a bimorph member having at least two piezoelectric members pasted together and polarized in the direction reverse to each other and said bimorph member is provided in the axial direction of said image transmitting means.

13. An endoscope system according to claim 1 or 6, further comprising a sensing means for sensing that said image receiving means is fitted to said eyepiece member and a control means for making said vibrating means operative only when said image receiving means is fitted to said eyepiece member in response to an output of said sensing means.

14. An endoscope system according to claim 3, wherein said vibrating means has a driving means for vibrating said image transmitting means in an eyepiece side portion and said driving means vibrates said image transmitting means in an eyepiece side portion at a frequency corresponding to a charge accumulating period of respective pixels of said solid state imaging device.

15. An endoscope system according to claim 14, wherein, in case said solid state imaging device is in a field accumulating mode, a frequency of said vibration driving means vibration is a field frequency.

16. An endoscope according to claim 14, wherein, in case said solid state imaging device is in a frame accumulating mode, a frequency of the said driving means vibration is a frame frequency.

17. An endoscope system according to claim 14, wherein, in case said solid state imaging device is for black and white, a driving means vibration amplitude is one pitch of said pixel arrangement of said solid state imaging device.

18. An endoscope system according to claim 14, wherein, in case said solid state imaging device is for colors having a color filter array on a front surface, thereof said driving means vibration amplitude is ½ repeating pitch of a color filter in said color filter array.

19. An endoscope system according to claim 1, further comprising a moiré fringe erasing low pass filter provided between an eyepiece side portion of said image transmitting means and said image receiving portion, said vibrating means for vibrating in a direction different from a moiré fringe erasing direction by a low pass filter.

20. An endoscope system according to claim 3, wherein said vibrating means has a driving means for vibrating said solid state imaging device in a direction intersecting substantially at right angles with an optical axis.

21. An endoscope system according to claim 20, further comprising a means for relatively vibrating in the same direction said image transmitting means on an objective side portion and an image formed on said end surface and synchronized with said solid state imaging device vibration.

22. An endoscope system according to claim 4, wherein said vibrating means has a driving means for vibrating said second image transmitting means in an image receiving side portion in the direction intersecting substantially at right angles with an optical axis.

23. An endoscope system according to claim 22, further comprising a driving means for vibrating said second image transmitting means in an exit side portion and synchronized with said second image transmitting means vibration in said image receiving side portion.

24. An endoscope system according to claim 23, further comprising an electric power feeding line means for feeding an electric power to said driving means for vibrating said second image transmitting means in an image receiving side portion and said driving means for vibrating said second image transmitting means in an exit side portion through said endoscope.

25. An endoscope system according to claim 23, further comprising a means for vibrating said image transmitting means of said endoscope in an objective side portion and an eyepiece said portion as synchronized with said second image transmitting means vibration in the image receiving side portion and exit side portion.

26. An endoscope system comprising:
an endoscope having an elongated insertable member, an objective optical system provided in a tip portion of said insertable member, an eyepiece portion provided on a rear end portion of said insertable member and an image transmitting means having a fiber bundle means for transmitting to said eyepiece portion an image formed by said objective optical system;
an image receiving means having an image receiving portion of many pixels on which an image from said eyepiece portion is formed and fitted to said eyepiece of said endoscope;
a moiré fringe erasing low pass filter means provided between an eyepiece side surface of said image transmitting means and said image receiving portion; and
a means for rotating said low pass filter means.

* * * * *

UNITED STATES PATENT AND TRADEMARK OFFICE
CERTIFICATE OF CORRECTION

PATENT NO.   :   4,870,950
DATED        :   October 3, 1989
INVENTOR(S)  :   KANBARA et al It is certified that error appears in the above-identified patent and that said Letters Patent is hereby corrected as shown below:

On the cover page, after Item [76], insert:

--[73]  Assignee:  Olympus Optical Co., Ltd., Tokyo, Japan--.

Signed and Sealed this

Nineteenth Day of February, 199

Attest:

HARRY F. MANBECK, JR.

Attesting Officer

Commissioner of Patents and Trademarks